US009308239B2

(12) United States Patent
Thiboutot et al.

(10) Patent No.: US 9,308,239 B2
(45) Date of Patent: Apr. 12, 2016

(54) METHODS AND COMPOSITIONS FOR TREATMENT OF RETINOID-RESPONSIVE CONDITIONS

(75) Inventors: Diane Thiboutot, Hershey, PA (US); Amanda Nelson, Hummelstown, PA (US); Kimberly Lumsden, Camp Hill, PA (US)

(73) Assignee: The Penn State Research Foundation, University Park, PA (US)

( * ) Notice: Subject to any disclaimer, the term of this patent is extended or adjusted under 35 U.S.C. 154(b) by 1675 days.

(21) Appl. No.: 12/393,331

(22) Filed: Feb. 26, 2009

(65) Prior Publication Data

US 2009/0311213 A1 Dec. 17, 2009

Related U.S. Application Data

(60) Provisional application No. 61/031,475, filed on Feb. 26, 2008, provisional application No. 61/103,724, filed on Oct. 8, 2008.

(51) Int. Cl.
| | |
|---|---|
| *A61K 38/19* | (2006.01) |
| *A61K 38/20* | (2006.01) |
| *A61K 31/575* | (2006.01) |
| *A61K 38/17* | (2006.01) |
| *A61K 38/16* | (2006.01) |
| *A61P 17/00* | (2006.01) |
| *A61P 31/04* | (2006.01) |

(52) U.S. Cl.
CPC ............... *A61K 38/20* (2013.01); *A61K 31/575* (2013.01); *A61K 38/1709* (2013.01); *A61K 38/191* (2013.01); *A61K 38/2006* (2013.01)

(58) Field of Classification Search
None
See application file for complete search history.

(56) References Cited

PUBLICATIONS

Crystal, R. Science, 1995, vol. 270, pp. 404-410.*
Rubanyi, biol. Aspects Med. (2001) 22:113-142.*
Juengst, British Medical Journal (2003) vol. 326, pp. 1410-1411.*
Chakraborty et al, intechopen, Oct. 2011, chapter 16, pp. 345-368.*
Nelson et al, The Journal of Clinical Investigation, vol. 118, No. 4, 2008, pp. 1468-1478.*
Akerstrom, B. et al., Lipocalins: unity in diversity, *Biochimica et Biophysica Acta*, 1482: 1-8, 2000.
Allenby, G. et al., retinoic acid receptors and retinoid X receptors: Interactions with endogenous retinoic acids, *Proc Natl Acad Sci USA*, 90: 30-34, Jan. 1993.
Baron, J. et al., Retinoic Acid and its 4-Oxo Metabolites are Functionally Active in Human Skin Cells In Vitro, *Journal of Investigative Dermatology*, 125: 143-153, Jul. 1, 2005.
Bickers, D. et al., The burden of skin diseases: 2004, *Journal of American Academy of Dermatology*, 55(3): 490-500, Sep. 2006.
Caramuta, S. et al., Regulation of lipocalin-2 gene by the cancer chemopreventive retinoid 4-HPR, *International Journal of Cancer*, 119: 1599-1606, 2006.
Coates, P. et al., Efficacy of oral isotretinion in the control of skin and nasal colonization by antibiotic-resistant propionibacteria in patients with acne, *British Journal of Dermatology*, 153: 1126-1136, 2005.
Cowland, J. et al., Neutrophil Gelatinase-Associated Lipocalin is Up-Regulated in Human Epithelial Cells by IL-1β, but not by TNF-$\alpha^1$, *The Journal of Immunology*, 171: 6630-6639, 2003.
Devireddy, L. et al., A Cell-Surface Receptor for Lipocalin 24p3 Selectivity Mediates Apoptosis and Iron Uptake, *Cell*, 123: 1293-1305, Dec. 29, 2005.
DiSepio, D. et al., Identification and characterization of a retinoid-induced class II tumor suppressor/growth regulatory gene, *Proc Natl Aced Sci USA*, 95: 14811-14815, Dec. 1998.
Draper, D. et al., Toll-like receptor 2-dependent and -independent activation of macrophages by group B *streptococci*, *Immunology Letters*, 102: 202-214, 2006.
Eckert, R. et al., S100 Proteins in the Epidermis, *The Journal of Investigative Dermatology*, 123: 23-33, 2004.
Flo, T. et al., Lipocalin 2 mediates an innate immune response to bacterial infection by sequestrating iron, *Nature*, 432: 917-921, Dec. 16, 2004.
Fujino, R. et al., Spermatogonial Cell-Mediated Activation of an IκBζ-Independent Nuclear Factor-κB Pathway in Sertoli Cells Induces Transcription of the Lipocalin-2 Gene, *Molecular Endocrinology*, 20(4):904-915, Apr. 2006.
Gläaser, R. et al., Antimicrobial psoriasin (S100A7) protects human skin from *Escherichia coli* infection, *Nature Immunology*, 6(1): 57-64, Jan. 2005.
Goldstein, J. et al., Isotretinion in the Treatment of Acne, *Archives of Dermatology*, 118: 555-558, Aug. 1982.
Goldstein, J. et al., Comparative effect of isotretinoin and etretinate on acne and sebaceous gland secretion, *Journal of the American Academy of Dermatology*, 6(4) Part 2: 760-765, Apr. 1982.
Gomez, E. et al., Effect of 13-cis-Retinoic Acid on the Hamster Flank Organ, *The Journal of Investigative Dermatology*, 74(6): 392-397, 1980.
Hanel, J. et al., Lipocalin 2 Diminishes Invasiveness and Metastasis of Ras-transformed Cells, *The Journal of Biological Chemistry*, 280(14): 13641-13647, Apr. 8, 2005.
Kalali, B. et at., Double-Stranded RNA Induces an Antiviral Defense Status in Epidermal Keratinocytes through TLR3-, PKR- and MDA5/RIG-I-Mediated Differential Signaling, *The Journal of Immunology*, 181: 2694-2704, 2008.
Kang, S. et al., Inflammation and Extracellular Matrix Degradation Mediated by Activated Transcription Factors Nuclear Factor-κB and Activator Protein-1 in Inflammatory Acne Lesions In Vivo, *American Journal of Pathology*, 106(6): 1691-1699, Jun. 2005.

(Continued)

*Primary Examiner* — Bridget E Bunner
*Assistant Examiner* — Fozia Hamud
(74) *Attorney, Agent, or Firm* — Dinsmore & Shohl LLP

(57) ABSTRACT

Methods and composition for treating a retinoid-responsive condition in a subject are provided according to embodiments of the present invention which include administering a therapeutically effective amount of a substance selected from the group consisting of: neutrophil gelatinase-associated lipocalin (NGAL), an NGAL analog, an NGAL stimulator and an analog of an NGAL stimulator, to a subject having a retinoid-responsive condition. Retinoid-responsive conditions illustratively include acne, rosacea, psoriasis, promyelocytic leukemia and neuroblastoma.

5 Claims, 10 Drawing Sheets

(56) References Cited

PUBLICATIONS

Kim, J. et al., Activation of Toll-Like Receptor 2 in Acne Triggers Inflammatory Cytokine Responses, *The Journal of Immunology*, 169: 1535-1541, 2002.

Kjeldsen, L. et al., Human neutrophil gelatinase-associated lipocalin and homologous proteins in rat and mouse, *Biochimica et Biophysica Acta*, 1482: 272-283.

Kjeldsen, L. et al., Identification of neutrophil gelatinase-associated lipocalin as a novel matrix protein of specific granules in human neutrophils, *Blood*, 83(3): 799-807, Feb. 1, 1994.

Leyden, J. et al., Qualitative and Quantitative Changes in Cutaneous Bacteria Associated with Systemic Isotretinoin Therapy for Acne Conglobata, *Journal of Investigatie Dermatology*, 86(4): 390-393, Apr. 1986.

Li, P. et al., Mouse 24p3 Protein Has an Effect on L929 Cell Viability, *International Journal of Biological Sciences*, 3(2): 100-107, 2007.

Lin, H. et al., Apoptosis induced by uterine 24p3 protein in endometrial carcinoma cell line, *Toxicology*, 234: 203-215, 2007.

Lögdberg, L. et al., Immunocalins: a lipocalin subfamily that modulates immune and inflammatory responses, *Biochimica et Biophysica Acta*, 1482: 284-297, 2000.

Mallbris, L. et al., neutrophil gelatinase-associated lipocalin is a marker for dysregulated keratinocyte differentiation in human skin, *Experimental Dermatology*, 11: 584-591, 2002.

Mishra, J. et al., Identification of neutrophil Gelatinase-Associated Lipocalin as a Novel Early Urinary Biomarker for Ischemic Renal Injury, *Journal of the American Society of Nephrology*, 14: 2534-2543, 2003.

Nelson, A. et al., 13-cis Retinoic Acid Induces Apoptosis and Cell Cycle Arrest in Human SEB-1 Sebocytes, *Journal of Investigative Dermatology*, 126: 2178-2189, 2006.

Newcomer, M. et al., Plasma retinol binding protein: structure and function of the prototypic lipocalin, *Biochimica et Biophysica Acta*, 1482: 57-64, 2000.

Ochoa, W. et al., Retinoic Acid Binds to the C2-Domain of Protein Kinase Cα, *Biochemistry*, 42: 8774-8779, 2003.

Reynolds, C. et al., Retinoid therapy of high-risk neuroblastoma, *Cancer Letters*, 197: 185-192, 2003.

Landthaler, M. et al., Inhibitory Effects of 13-cis-retinoic Acid on Human Sebaceous Glands, *Arch Dermatol Res*, 269(3): 297-309, 1980.

Peck, G. et al., Prolonged Remissions of cystic and Conglobate Acne with 13-cis-Retinoic Acid, *The New England Journal of Medicine*, 300(7): 329-333, Feb. 15, 1979.

Pettersson, F. et al., Enhanced retinoid-induced apoptosis of MDA-MB-231 breast cancer cells by PKC inhibitors involves activation of ERK, Oncogene, 23: 7053-7066, 2004.

Sen, G. et al., Hitching RIG to action, *Nature Immunology*, 6(11): 1074-1076, Nov. 2005.

Seo, S. et al., Expression of Neutrophil Gelatinase-Associated Lipocalin in Skin Epidermis, *journal of Investigative Dermatology*, 126: 510-512, 2006.

Silverman, G. at al., The Serpins are an Expanding Superfamliy of Structurally Similar but Functionally Diverse Proteins, *The Journal of Biological Chemistry*, 276(36): 33293-33296, Sep. 7, 2001.

Strauss, J. et al., The Effect of Marked Inhibition of Sebum Production with 13Cis-retinoic Acid on Skin Surface Lipid Composition, *The Journal of Investigative Dermatology*, 74(2): 66-67, 1980.

Thiboutot, D. et al., Human Skin is a Steroidogenic Tissue: Steroidogenic Enzymes and Cofactors are Expressed in Epidermis, Normal Sebocytes, and an Immoralized Sebocyte Cell Line (SEB-1), *Journal of Investigative Dermatology*, 120(6): 905-914, Jun. 2003.

Trivedi, N. et al., Gene Array Expression Profiling in Acne Lesions Reveals Marked Upregulation of Genes Involved in Inflammation and Martrix Remodeling, *Journal of Investigative Dermatology*, 126: 1071-1079, 2006.

Tsukada, M. et al., 13-cis Retinoic Acid Exerts its Specific Activity on Human Sebocytes through Selective Intracellular Isomerization to All-trans Retinoic Acid and Binding to Retinoid Acid Receptors, *Journal of Investigative Dermatology*, 115(2): 321-327, Aug. 2000.

Vijay-Kumar M. et al., Protein Kinase R Mediates Intestinal Epithelial Gene Remodeling in Response to Double-Stranded RNA and Live Rotavirus, *The Journal of Immunology*, 174: 6322-6331, 2005.

Yamasaki, K. et al., Increased serine protease activity and cathelicidin promotes skin inflammation in rosacea, *Nature Medicine*, 13(8): 975-980, Aug. 2007.

Yan, L. et al., The High Molecular Weight Urinary Matrix Metalloproteinase (MMP) Activity is a Complex of Gelatinase B/MMP-9 and Neutrophil Gelatinase-associated Lipocalin (NGAL), *The Journal of Biological Chemistry*, 276(40): 37258-37265, Oct. 5, 2001.

Yang, J. et al., An Iron Delivery Pathway Mediated by a Lipocalin, *Molecular Cell*, 10: 1045-1056, Nov. 2002.

Yoneyama, M. et al., The RNA helicase RIG-I has an essential function in double-stranded RNA-induced innate antiviral responses, *Nature Immunology*, 5(7): 730-737, Jul. 2004.

Ziegler, S. et al., Lipocalin 24p3 is regulated by the Wnt pathway independent of regulation by iron, *Cancer Genetics and Cytogenetics*, 174: 16-23, 2007.

Nagpal, S. et al., T1G1 and T1G2 (Tazarotene Induced Genes 1 and 2) are Novel Retinoic Acid Receptor-Responsive Genes in Skin, *The Journal of Investigative Dermatology Abstracts*, 106: 818, 1996.

\* cited by examiner

A QPCR

B Western

A

B

METHODS AND COMPOSITIONS FOR TREATMENT OF RETINOID-RESPONSIVE CONDITIONS

REFERENCE TO RELATED APPLICATIONS

This application claims priority from U.S. Provisional Patent Application Ser. Nos. 61/031,475, filed Feb. 26, 2008 and 61/103,724, filed Oct. 8, 2008, the entire content of both of which is incorporated herein by reference.

GOVERNMENT SPONSORSHIP

This invention was made with government support under RO1 AR47820 awarded by NIAMS NIH. The government has certain rights in the invention.

FIELD OF THE INVENTION

Described are compositions and methods generally relating to treatment of retinoid-responsive conditions in a subject. In specific embodiments, compositions and methods described herein relate to neutrophil gelatinase-associated lipocalin, analogs and stimulators thereof, and their use in treatment of retinoid-responsive conditions in a subject.

BACKGROUND OF THE INVENTION

A number of pathological conditions, illustratively including acne, rosacea, psoriasis, promyelocytic leukemia and neuroblastoma, are currently treated using retinoids and are considered retinoid-responsive conditions.

For example, acne is the most prevalent skin condition encountered by dermatologists, affecting nearly 85% of the people between the ages of 12 and 24 years (15). While acne is not life-threatening, it does have significant physical and psychosocial morbidity (16). Acne results from the interplay of 4 factors: increased production sebum by the sebaceous gland, altered keratinization of follicular keratinocytes, activity of *Propionibacterium acnes* (*P. acnes*) and inflammation. *P. acnes* contributes to the inflammation associated with acne via activation of Toll-like receptor 2 on the surface of inflammatory cells in the skin infiltrate (17).

Isotretinoin (13-cis RA) is the most potent agent that affects all the pathogenic features of acne. It is the only therapeutic agent that drastically reduces the size and secretion of sebaceous glands. However, isotretinoin, like thalidomide, is a teratogen and its use is closely regulated through an FDA-mandated risk management program called iPLEDGE.

There is a continuing need for methods and compositions to treat retinoid-responsive conditions.

SUMMARY OF THE INVENTION

Methods of treating a retinoid-responsive condition in a subject are provided according to embodiments of the present invention which include administering a therapeutically effective amount of a substance selected from the group consisting of: neutrophil gelatinase-associated lipocalin (NGAL), an NGAL analog, an NGAL stimulator and an analog of an NGAL stimulator; to a subject having a retinoid-responsive condition. Optionally, the NGAL analog is an NGAL receptor agonist. In a further option, the NGAL stimulator is selected from the group consisting of: a Toll-like receptor 2 ligand, a Toll-like receptor 3 ligand, an activator of NFκB, leukotriene B4, cholesterol oleate and IL-17. Exemplary activators of NFκB that can be used in methods of treatment of retinoid-responsive conditions include IL1-beta and TNF-alpha. IL1-beta and TNF-alpha can be used individually or in combination.

Retinoid-responsive conditions are well-known in the art and include acne, rosacea, psoriasis, promyelocytic leukemia and neuroblastoma. In embodiments of methods of the present invention, the protein is administered to skin affected by: acne, rosacea and/or psoriasis. In further embodiments, the protein is administered to sebaceous glands of a subject affected by: acne, rosacea and/or psoriasis.

An exemplary Toll-like receptor 2 ligand used in embodiments of methods of the present invention is N-palmitoyl-S-[2,3-bis(palmitoyloxy)-(2RS)-propyl]-[R]-cysteinyl-[S]-seryl-[S]-lysyl-[S]-lysyl-[S]-lysyl-[S]-lysine. An exemplary Toll-like receptor 3 ligand used in embodiments of methods of the present invention is polyinosinic:polycytidylic acid.

Methods of treating a retinoid-responsive condition in a subject according to embodiments of the present invention include stimulating NEAL expression in a subject having a retinoid responsive condition. Methods of treating acne, rosacea, psoriasis, promyelocytic leukemia or neuroblastoma in a subject according to embodiments of the present invention include stimulating NGAL expression in a subject having acne, rosacea, psoriasis, promyelocytic leukemia or neuroblastoma. In embodiments of methods of the present invention, NGAL expression is stimulated by administration of an NGAL stimulator which upregulates transcription of a gene encoding NGAL and/or increases translation of NGAL, to increase NGAL protein, to a subject having a retinoid responsive condition. Optionally, NGAL expression is stimulated by administration of a nucleic acid encoding NGAL to the subject.

An NGAL stimulator used in treatment of a retinoid-responsive condition is selected from the group consisting of: a Toll-like receptor 2 ligand, a Toll-like receptor 3 ligand, an activator of NFκB, leukotriene B4, cholesterol oleate and IL-17 according to embodiments of methods of the present invention. In particular embodiments, the activator of NFκB is IL1-beta. TNF-alpha or a combination thereof. An exemplary Toll-like receptor 2 ligand used in treatment of a retinoid-responsive condition according to embodiments of the present invention is N-Palmitoyl-S-[2,3-bis(palmitoyloxy)-(2RS)-propyl]-[R]-cysteinyl-[S]-seryl-[S]-lysyl-[S]-lysyl-[S]-lysyl-[S]-lysine. An exemplary Toll-like receptor 3 ligand used in treatment of a retinoid-responsive condition according to embodiments of the present invention is polyinosinic:polycytidylic acid.

Methods of treating retinoid-responsive condition in a subject are provided according to embodiments of the present invention which include administering a therapeutically effective amount of a protein selected from: a protein comprising the amino acid of SEQ ID No. 1; a protein comprising the amino acid of SEQ ID No. 2; a protein encoded by the complement of a nucleic acid that hybridizes under highly stringent conditions with the nucleotide sequence of SEQ ID No 3; a protein encoded by the complement of a nucleic acid that hybridizes under highly stringent conditions with the nucleotide sequence of SEQ ID No. 4; wherein the highly stringent conditions are: hybridization in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes; a protein comprising an amino acid sequence that is at least 95% identical to SEQ ID No. 1; and a protein comprising an amino acid sequence that is at least 95% identical to SEQ ID No. 2, to a subject having a retinoid-responsive condition.

Methods of inhibiting *Propionibacterium acnes* are provided according to methods of the present invention which include contacting a *Propionibacterium acnes* bacterium with a substance selected from the group consisting of: NGAL and an NGAL analog. In preferred embodiments, the *Propionibacterium acnes* bacterium is in contact with a human subject, such as a subject having acne, rosacea or a predisposition to having acne or rosacea.

In further embodiments, methods of inhibiting *Propionibacterium acnes* are provided according to the present invention which include administering an NGAL stimulator and/or an analog of an NGAL stimulator to a subject colonized by *Propionibacterium acnes* or having a predisposition to colonization by *Propionibacterium acnes*.

Compositions are provided according to embodiments of the present invention which include neutrophil gelatinase-associated lipocalin (NGAL), an NGAL analog, an NGAL stimulator or an analog of an NGAL stimulator. A combination of two or more of neutrophil gelatinase-associated lipocalin (NGAL), an NGAL analog, an NGAL stimulator and an analog of an NGAL stimulator can be included in compositions according to embodiments of the present invention Compositions according to embodiments of the present invention optionally include a pharmaceutically acceptable carrier. NGAL stimulators included in compositions according to embodiments of the present invention can be a Toll-like receptor 2 ligand, a Toll-like receptor 3 ligand, an activator of NFκB, N-Palmitoyl-S-[2,3-bis(palmitoyloxy)-(2RS)-propyl]-[R]-cysteinyl-[S]-seryl-[S]-lysyl-[S]-lysyl-[S]-lysyl-[S]-lysine, polyinosinic:polycytidylic acid, leukotriene B4, cholesterol oleate or IL-17. A combination of two or more of a Toll-like receptor 2 ligand, a Toll-like receptor 3 ligand, an activator of NFκB, leukotriene B4, N-Palmitoyl-S-[2,3-bis(palmitoyloxy)-(2RS)-propyl]-[R]-cysteinyl-[S]-seryl-[S]-lysyl-[S]-lysyl-[S]-lysyl-[S]-lysine, polyinosinic:polycytidylic acid, cholesterol oleate or IL-17 can be included in compositions according to embodiments of the present invention. In further embodiments, compositions according to the present invention include a protein selected from: a protein comprising the amino acid of SEQ ID No. 1; a protein comprising the amino acid of SEQ ID No. 2; a protein encoded by the complement of a nucleic acid that hybridizes under highly stringent conditions with the nucleotide sequence of SEQ ID No. 3; a protein encoded by the complement of a nucleic acid that hybridizes under highly stringent conditions with the nucleotide sequence of SEQ ID No. 4; wherein the highly stringent conditions are: hybridization in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes; a protein comprising an amino acid sequence that is at least 95% identical to SEQ ID No. 1; and a protein comprising an amino acid sequence that is at least 95% identical to SEQ ID No. 2, to a subject having a retinoid-responsive condition.

In still further embodiments, compositions and methods according to the present invention include a protein selected from: a protein comprising the amino acid of SEQ ID No. 1; a protein comprising the amino acid of SEQ ID No. 2; a protein encoded by the complement of a nucleic acid that hybridizes under highly stringent conditions with nucleotides 74-670 of the nucleotide sequence of SEQ ID No. 3; a protein encoded by the complement of a nucleic acid that hybridizes under highly stringent conditions with nucleotides 23-625 of the nucleotide sequence of SEQ ID No. 4; wherein the highly stringent conditions are: hybridization in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes; a protein comprising an amino acid sequence that is at least 95% identical to SEQ ID No. 1; and a protein comprising an amino acid sequence that is at least 95% identical to SEQ ID No. 2, to a subject having a retinoid-responsive condition.

DETAILED DESCRIPTION OF THE INVENTION

Figure 1:
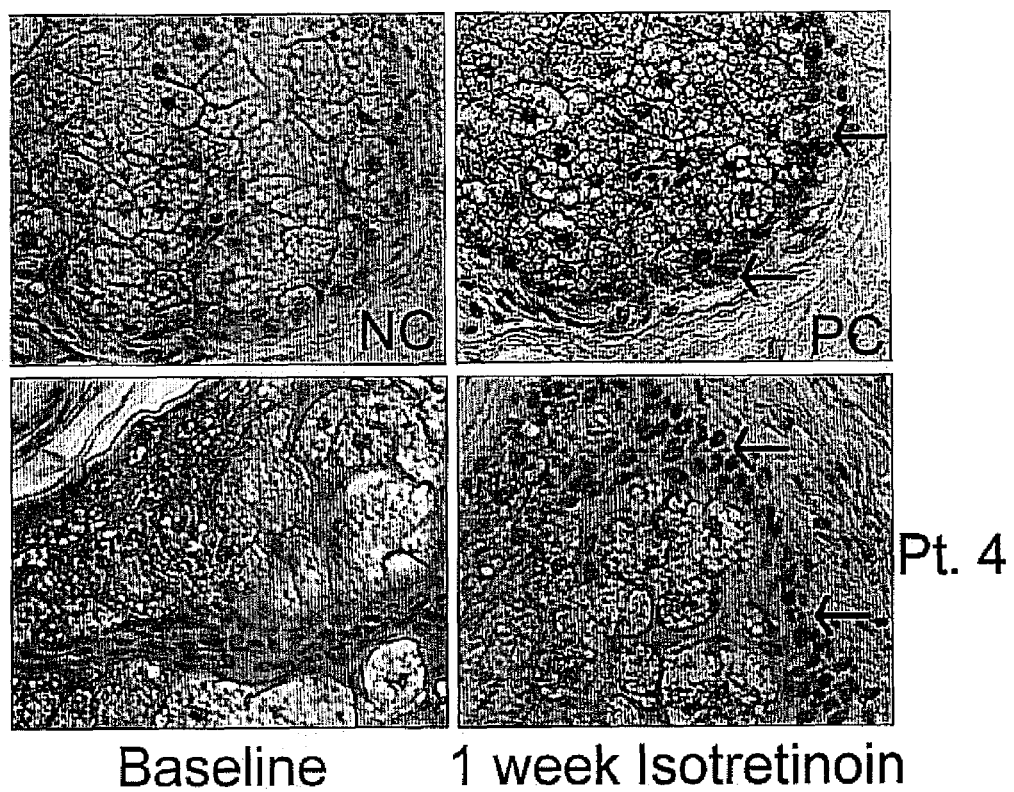
FIG. 1 is a reproduction of images showing representative TUNEL stained sections from Patient 4 taken at baseline and at one week of isotretinoin treatment.

Methods and compositions relating to neutrophil gelatinase-associated lipocalin (NGAL, also referred to as lipocalin 2 and LCN2), NGAL analogs, and use of NGAL and NGAL analogs, are provided according to embodiments of the present invention for treatment of retinoid-responsive conditions. Methods and compositions relating to increasing levels and/or activity of NGAL and/or NGAL analogs, and use of substances which increase levels and/or activity of NGAL and/or NGAL analogs, are provided according to embodiments of the present invention for treatment of retinoid-responsive conditions.

The term "retinoid-responsive condition" refers to any disease or condition for which administration of one or more retinoids has a beneficial effect. Retinoid-responsive conditions that can be treated using compositions and methods of the present invention include, but are not limited to, inflammatory dermatological conditions including, but not limited to, acne, rosacea, urticaria, eczema and psoriasis; and proliferative disorders including, but not limited to, promyelocytic leukemia and neuroblastoma.

Retinoids are well-known in the art and include retinol, retinal, tretinoin, isotretinoin, alitretinoin, etretinate, acitretin, tazarotene, bexarotene and adapalene.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; and B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004.

NGAL is a protein which was initially isolated from neutrophils as described in references 27-32.

The term "NGAL" refers to NGAL protein disclosed herein and orthologs from any species. The term "NGAL analog" refers to a substance having a functional characteristic of NGAL. In particular, an NGAL analog is effective to produce a desired physiologic or pharmacologic effect in a subject having a retinoid-responsive pathological condition, prevents or ameliorates a retinoid-responsive pathological condition in the subject. In further embodiments, an NGAL analog is effective to inhibit *Propionibacterium acnes*.

NGAL used in methods according to embodiments of the present invention and included in compositions according to embodiments of the present invention can be apo-NGAL or holo-NGAL.

In embodiments of the present invention the term "NGAL" refers to proteins of SEQ ID Nos. 1 and 2 and analogs thereof which have a desired NGAL function, particularly inhibition of *P. acnes* and/or apoptotic activity in sebocytes.

Human NGAL is disclosed herein as SEQ ID No. 1:

```
                                              (SEQ ID No. 1)
MPLGLLWLGLALLGALHAQAQDSTSDLIPAPPLSKVPLQQNFQDNQFQGK

WYVVGLAGNAILREDKDPQKMYATIYELKEDKSYNVTSVLFRKKKCDYWI

RTFVPGCQPGEFTLGNIKSYPGLTSYLVRVVSTNYNQHAMVFFKKVSQNR

EYFKITLYGRTKELTSELKENFIRFSKSLGLPENHIVFPVPIDQCIDG
```

Mouse NGAL is disclosed herein as SEQ ID No. 2:

```
                                              (SEQ ID No. 2)
MALSVMCLGLALLGVLQSQAQDSTQNLIPAPSLLTVPLQPDFRSDQFRGR

WYVVGLAGNAVQKKTEGSFTMYSTIYELQENNSYNVTSILVRDQDQGCRY
```

```
-continued
WIRTFVPSSRAGQFTLGNMHRYPQVQSYNVQVATTDYNQFAMVFFRKTSE

NKQYFKITLYGRTKELSPELKERFTRFAKSLGLKDDNIIFSVPTDQCIDN
```

As used herein, the term "NGAL analog" refers to both naturally occurring variations of a given NGAL protein and recombinantly prepared mutations of a given NGAL protein, as well as functional fragments thereof.

The term "NGAL analog" refers to a protein characterized by an amino acid sequence substantially similar to the amino acid sequence of human NGAL (SEQ ID No. 1) or mouse NGAL (SEQ ID No. 2) and which has substantially similar functional properties compared to human NGAL or mouse NGAL. Substantially similar analogs of human NGAL or mouse NGAL have at least 80%, or at least 85%, 90%, 91%, 92%, 93%, 94%, 95%, 96%, 97%, 98%, 99%, or greater, amino acid sequence identity to human NGAL or mouse NGAL. An NGAL analog can be encoded by a nucleic acid sequence having substantial similarity to nucleic acid sequences encoding human NGAL and mouse NGAL disclosed herein. A nucleic acid sequence having substantial similarity to a nucleic acid sequence encoding human NGAL or mouse NGAL has at least 70%, at least 75%, or at least 85%, 90%, 91%, 92%, 93%, 94%, 95%, 96%, 97%, 98%, 99%, or greater, nucleic acid sequence identity to nucleic acid sequences encoding human NGAL or mouse NGAL.

In embodiments of the present invention, a substantially similar nucleic acid sequence is characterized as having a complementary nucleic acid sequence capable of hybridizing to a nucleic acid sequence encoding human NGAL or mouse NGAL under high stringency hybridization conditions.

The term "nucleic acid" as used herein refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone. Under highly stringent conditions, SEQ ID No. 3 or SEQ ID No. 4 will hybridize to the complement of substantially identical targets and not to unrelated sequences. In preferred embodiments, under highly stringent conditions, at least the coding region of SEQ ID No. 3 (nucleotides 74-670) or SEQ ID No. 4 (nucleotides 23-625) will hybridize to the complement of substantially identical targets and not to unrelated sequences.

Mutations can be introduced using standard molecular biology techniques, such as site-directed mutagenesis and PCR-mediated mutagenesis. One of skill in the art will recognize that one or more amino acid mutations can be introduced without altering the functional properties of NGAL. For example, one or more amino acid substitutions, additions, or deletions can be made without altering the functional properties of NGAL.

Conservative amino acid substitutions can be made in NGAL proteins to produce NGAL analogs. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

NGAL analogs can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

Embodiments of methods and compositions of the present invention include NGAL proteins having at least 90%, 91%, 92%, 93%, 94%, 95%, 96%, 97%, 98% or 99% amino acid sequence identity to SEQ ID No. 1 or SEQ ID No.2.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12 and a gap penalty of 4 is used.

The percent identity between two sequences is determined using techniques similar to those described above, with or without allowing gaps. In calculating percent identity, typically only exact matches are counted.

NGAL can be produced in recombinant host cells using well-known conventional techniques. Broadly described, a nucleic acid molecule encoding NGAL is operably linked to regulatory sequences that control transcriptional expression in an expression vector. The expression vector is introduced into a host cell where it is expressed and the NGAL can then be isolated.

An expression vector including a nucleic acid encoding NGAL is administered to a subject to treat a retinoic-acid responsive condition according to embodiments of the present invention.

NGAL of SEQ ID No. 1 is encoded by nucleotides 74-670 of the human NGAL mRNA of SEQ ID No. 3:

```
  1 actcgccacc tcctcttcca cecelgecag gcccagcagc caccacagcg cctgcttcct
 61 cggccctgaa atcatgcccc taggtctcct gtggctgggc ctagccctgt tggggctct
121 gcatgcccag gcccaggact ccacctcaga cctgatccca gccccacctc tgagcaaggt
181 ccctctgcag cagaacttcc aggacaacca attccagggg aagtggtatg tggtaggcct
241 ggcagggaat gcaattctca gagaagacaa agacccgcaa aagatgtatg ccaccatcta
301 tgagctgaaa gaagacaaga gctacaatgt cacctccgtc ctgtttagga aaagaagtg
361 tgactactgg atcaggactt ttgttccagg ttgccagccc ggcgagttca cgctgggcaa
421 cattaagagt taccctggat taacgagtta cctcgtccga gtggtgagca ccaactacaa
481 ccagcatgct atggtgttct tcaagaaagr ttctcaaaac agggagtact tcaagatcac
541 cctctacggg agaaccaagg agctgacttc ggaactaaag gagaacttca tccgcttctc
601 caaatctctg ggcctccctg aaaaccacat cgtcttccct gtcccaatcg accagtgtat
661 cgacggctga gtgcacaggt gccgccagct gccgcaccag cccgaacacc attgagggag
721 ctgggagacc ctccccacag tgccacccat gcagctgctc cccaggccac cccgctgatg
781 gagccccacc ttgtctgcta aataaacatg tgccctcagg ccaaaaaaaa aaaaaaaaaa
```

NGAL of SEQ ID No. 2 is encoded by nucleotides 23-625 of the mouse NGAL mRNA of SEQ ID No. 4:

```
  1 agacctagta gctgtggaaa ccatggccct gagtgtcatg tgtctgggcc ttgccctgct
 61 tggggtcctg cagagccagg cccaggactc aactcagaac ttgatccctg ccccatctct
121 gctcactgtc cccctgcagc cagacttccg gagcgatcag ttccggggca ggtggtacgt
181 tgtgggcctg gcaggcaatg cggtccagaa aaaaacagaa ggcagcttta cgatgtacag
241 caccatctat gagctacaag agaacaatag ctacaatgtc acctccatcc tggtcaggga
301 ccaggaccag ggctgtcgct actggatcag aacatttgtt ccaagctcca gggctggcca
361 gttcactctg ggaaatatgc acaggtatcc tcaggtacag agctacaatg tgcaagtggc
421 caccacggac tacaaccagt tcgccatggt attttccga aagacttctg aaaacaagca
481 atacttcaaa attaccctgt atggaagaac caaggagctg tccctgaac tgaaggaacg
541 tttcaccgc tttgccaagt ctctgggcct caaggacgac aacatcatct tctctgtccc
601 caccgaccaa tgcattgaca actgaatggg tggtgagtgt ggctgactgg gatgcgcaga
661 gacccaatgg ttcaggcgct gcctgtctgt ctgccactcc atctttcctg ttgccagaga
721 gccacctggc tgccccacca gccaccatac caaggagcat ctggagcctc ttcttatttg
781 gccagcactc cccatccacc tgtcttaaca ccaccaatgg cgtccccttt ctgctgaata
841 aatacatgcc ccc
```

Non-limiting examples of regulatory sequences that control transcriptional expression in an expression vector illustratively include a promoter, an enhancer, a splicing signal, a transcription start site, a transcription termination signal, a polyadenylation signal, an internal ribosome entry site (IRES) and combinations of these or other regulatory sequences. A secretory sequence encoding a secretion signal that directs an encoded heterologous protein into the secretory pathway of a host cell is optionally included. Additional sequences optionally included in an expression vector include one or more sequences encoding a marker suitable for selection of cells carrying the expression vector.

Viral expression vectors can be used to express a desired protein. Non-limiting examples of virus expression systems include adenovirus, adeno-associated virus, herpes virus, vaccinia virus and lentivirus.

A host cell for expression of NGAL can be prokaryotic or eukaryotic, such as bacterial, plant, insect, fungus, yeast, and mammalian cells.

An expression vector is introduced into a host cell using well-known techniques such as infection or transfection, including calcium phosphate transfection, liposome-mediated transfection, electroporation and sonoporation. Expression constructs and methods for their generation and use to express a desired protein are known in the art, as described, for example, in Sambrook et al., Molecular Cloning: A Laboratory Manual, Cold Spring Harbor Laboratory Press, 2001; Ausubel, F. et al., (Eds.), Short Protocols in Molecular Biology, Wiley, 2002; and S. J. Higgins and B. D. Hames (Eds.), Protein Expression: A Practical Approach, Oxford University Press, USA, 1999.

In addition to recombinant methodology, chemical synthetic techniques can be used to produce NGAL. For example, NGAL can be produced using solid phase synthesis, solution phase synthesis, partial solid phase synthesis or fragment condensation.

The term "isolated" as used herein refers to a substance that has been separated from contaminating cellular components associated with the substance in nature not intended to be associated with the substance and that would interfere with use of the substance in therapeutic, prophylactic, diagnostic or other uses. Generally, an isolated substance described herein is at least about 80% pure, at least about 90% pure, at least about 95% pure, or greater than about 99% pure. Purification is achieved using well-known standard methodology such as fractionation and/or chromatography, such as ammonium sulfate precipitation and elution chromatography such as size exclusion chromatography, displacement chromatography, ion exchange chromatography and bioaffinity chromatography. Exemplary purification methodology is described in S. Doonan, Protein Purification Protocols Humana Press, 1996.

In embodiments of the present invention, isolated NGAL, an isolated NGAL analog, an isolated NGAL stimulator and/or an isolated analog of an NGAL stimulator is administered to a subject and/or included in a composition of the present invention.

A substance effective to increase NGAL and/or produce a therapeutic effect of NGAL in a subject is administered to a subject having a retinoid-responsive condition according to embodiments of the present invention.

The term "NGAL stimulator" refers to substances effective to increase NGAL in a subject, illustratively including expression vectors encoding NGAL, Toll-like receptor 2 (TLR2) ligands, Toll-like receptor 3 (TLR3) ligands, activators of NFκB, leukotriene B4, cholesterol oleate, and IL-17.

The term "analog of an NGAL stimulator" refers to structural variants of NGAL stimulators that are functional to increase NGAL in a subject.

A substance effective to produce a therapeutic effect of NGAL in a subject includes an NGAL receptor agonist. The term "NGAL receptor agonist" refers to a substance that interacts with a NGAL receptor and enhances or increases a function of the NGAL receptor. The term "NGAL receptor agonist" encompasses both full and partial NGAL receptor agonists.

The term "Toll-like receptor 2 ligand" refers to a substance that interacts with a Toll-like receptor 2 and enhances or increases a function of the Toll-like receptor 2. The term "Toll-like receptor 2 ligand" encompasses both full and partial Toll-like receptor 2 agonists.

The term "Toll-like receptor 3 ligand" refers to a substance that interacts with a Toll-like receptor 3 and enhances or increases a function of the Toll-like receptor 3. The term "Toll-like receptor 3 ligand" encompasses both full and partial Toll-like receptor 3 agonists.

The term "activator of NFκB" refers to a substance that increases activity of NFκB to stimulate transcription of NGAL. Non-limiting examples of substances that are activators of NFkB are IL1-beta and TNF-alpha.

In embodiments of methods and compositions of the present invention, a stimulator of NGAL expression is an NGAL ligand, a TLR2 ligand, TLR3 ligand, or NFkB activator. A combination of any two or more substances selected from a TLR2 ligand, a TLR3 ligand, and a NFkB activator can be used in embodiments of methods and compositions of the present invention.

In embodiments of methods and compositions of the present invention, an NGAL ligand, a TLR2 ligand, TLR3 ligand, or NFkB activator is a small molecule stimulator of NGAL expression. Small molecule stimulators of NGAL expression, such as NGAL ligands, TLR2 ligands, TLR3 ligands, and NFkB activators, are identified by screening of substances in an assay to determine an effect of a putative stimulator on NGAL expression. For example, naturally occurring or synthetic organic or inorganic substances having a molecular mass in the range of about 50-3000 Daltons, more preferably having a molecular mass in the range of about 100-2000 Daltons, and still more preferably having a molecular mass in the range of about 300-700 Daltons. Exemplary assays to identify small molecule stimulators of NGAL expression include contacting a cell which naturally or recombinantly expresses an NGAL receptor, TLR2, TLR3, and/or NFkB, with one or more putative small molecule stimulators and detecting a change in NGAL expression compared to untreated cells. Methods for detection of change in expression of a selected nucleic acid or protein are well-known in the art, illustratively including Northern blot, RNAse protection, RT-PCR and immunoassays. The term "stimulator of expression" refers to an increase in transcription and/or translation which increased levels and/or activity of NGAL.

The terms "treating" and "treatment" used to refer to treatment of a retinoid-responsive condition in a subject includes: preventing, inhibiting or ameliorating the retinoid-responsive condition in a subject, such as slowing progression of the condition and/or reducing or ameliorating a sign or symptom of the condition.

A subject treated according to methods and using compositions of the present invention can be mammalian or non-mammalian. Humans are preferred subjects treated according to methods and using compositions of the present invention, and a mammalian subject can be any mammal including, but not limited to, a non-human primate; a rodent such as a mouse, rat, or guinea pig; a domesticated pet such as a cat or dog; a horse, cow, pig, sheep, goat, or rabbit. A non-mammalian subject can be any non-mammal including, but not limited to, fish; and a bird such as a duck, goose, chicken, or turkey.

In a particular embodiment of the present invention a method of treating acne in a subject is provided which includes administering a therapeutically effective amount of NGAL, an NGAL analog, an NGAL stimulator or an analog of an NGAL stimulator to a subject having acne.

A therapeutically effective amount is an amount which produces a desired physiologic or pharmacologic effect in a subject, prevents or ameliorates a condition being treated in the subject. For example, a therapeutically effective amount is an amount which reduces or eliminates a sign or symptom of a retinoid-responsive condition being treated in the subject.

Suitable dosages ranges of NGAL, an NGAL analog, an NGAL stimulator or an analog of an NGAL stimulator depend on various factors such as the age of the subject, the severity and type of condition being treated in the subject, the general condition of the subject, the route and form of administration of the composition being administered and the particular composition administered. One of ordinary skill in the art will be able to ascertain a therapeutically effective amount without undue experimentation in view of the present disclosure and what is known in the art.

Administration of NGAL, an NGAL analog, an NGAL stimulator or an analog of an NGAL stimulator according to embodiments of a method of the present invention includes administration according to a dosage regimen to produce a desired response. For example, one or more dosage units of NGAL, an NGAL analog, an NGAL stimulator or an analog of an NGAL stimulator is administered to a subject at one time in particular embodiments. A suitable schedule for administration of doses depends on several factors including age, weight, gender, medical history and health status of the subject, type of composition used and route of administration, for example. One of skill in the art is able to readily determine a dose and schedule of administration for a particular subject.

Embodiments of the present invention optionally include administration of a pharmacologically active agent in addition to NGAL, an NGAL analog, an NGAL stimulator or an analog of an NGAL stimulator. Non-limiting examples of pharmacologically active agents administered in addition to NGAL, an NGAL analog, an NGAL stimulator or an analog of an NGAL stimulator, in combination or separately, according to embodiments of methods of the present invention include, antibiotics, antivirals, antineoplastic agents, analgesics, antipyretics, antidepressants, antipsychotics, anticancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents and vasoactive agents.

A pharmaceutically acceptable carrier can be included in a composition including NGAL, an NGAL analog, an NGAL stimulator or an analog of an NGAL stimulator. A pharmaceutically acceptable carrier is substantially non-toxic to the subject in amounts administered and has substantially no deleterious effects on any active component of a composition in which it is included.

The NGAL, an NGAL analog, an NGAL stimulator or an analog of an NGAL stimulator is formulated for topical, local and/or systemic administration to the subject.

Methods according to embodiments of the present invention include administration of NGAL, an NGAL analog, an NGAL stimulator or an analog of an NGAL stimulator as pharmaceutical formulations, including those suitable for oral, rectal, nasal, pulmonary, epidural, ocular, otic, intraarterial, intracardiac, intracerebroventricular, intracranial, intradermal, intravenous, intramuscular, intraperitoneal, intraosseous, intrathecal, intravesical, subcutaneous, topical, transdermal, and transmucosal, such as by sublingual, buccal, vaginal, and inhalational routes of administration.

A pharmaceutical formulation of NGAL, an NGAL analog, an NGAL stimulator or an analog of an NGAL stimulator according to embodiments of the present invention is in any dosage form suitable for administration to a subject, illustratively including solid, semi-solid and liquid dosage forms such as tablets, capsules, powders, granules, suppositories, pills, solutions, suspensions, ointments, lotions, creams, gels, pastes, sprays and aerosols.

Liposomes and emulsions are well-known types of pharmaceutical formulations that can be used to deliver a pharmaceutical agent, particularly a hydrophobic pharmaceutical agent. In embodiments of the present invention, liposomes are particles typically produced as a unilammellar bilayer or a multilammellar bilayer of amphipathic molecules enclosing an aqueous interior. Liposomes can include any type of amphipathic materials compatible with a composition to be delivered, illustratively including naturally-occurring lipids, synthetic lipids and combinations thereof.

A pharmaceutical formulation of a composition of the present invention can include a pharmaceutically acceptable carrier. The term "pharmaceutically acceptable carrier" refers to a carrier which is suitable for use in a subject without undue toxicity or irritation to the subject and which is compatible with other ingredients included in a pharmaceutical composition. Pharmaceutically acceptable carriers, methods for making pharmaceutical compositions and various dosage forms, as well as modes of administration are well-known in the art, for example as detailed in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

A solid dosage form for administration or for suspension in a liquid prior to administration illustratively includes capsules, tablets, powders, and granules. In such solid dosage forms, one or more active agents, is admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alignates, gelatin, polyvinylpyrrolidone, sucrose, and acacia; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, cetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, sorbic acid, gentamycin and phenol; and a stabilizer such as, for example, sucrose, EDTA, EGTA, and an antioxidant.

Solid dosage forms optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include one or more active agents and a pharmaceutically acceptable carrier formulated as an emulsion, solution, suspension, syrup, or elixir. A liquid dosage form of a composition of the present invention may include a colorant, a stabilizer, a wetting agent, an emulsifying agent, a suspending agent, a sweetener, a flavoring, or a perfuming agent.

For example, a composition for parenteral administration may be formulated as an injectable liquid. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, sucrose, EDTA, EGTA, and an antioxidant.

For topical administration, a composition can be formulated for administration to the skin such as for local effect, and/or as a "patch" formulation for transdermal delivery. Pharmaceutical formulations suitable for topical administration include, for example, ointments, lotions, creams, gels, pastes, sprays and powders. Ointments, lotions, creams, gels and pastes can include, in addition to one or more active agents, a base such as an absorption base, water-removable base, water-soluble base or oleaginous base and excipients such as a thickening agent, a gelling agent, a colorant, a stabilizer, an emulsifying agent, a suspending agent, a sweetener, a flavoring, or a perfuming agent.

Transdermal formulations can include percutaneous absorption enhancers such as acetone, azone, dimethyl acetamide, dimethyl formamide, dimethyl sulfoxide, ethanol, oleic acid, polyethylene glycol, propylene glycol and sodium lauryl sulfate. Ionotophoresis and/or sonophoresis can be used to enhance transdermal delivery.

Powders and sprays for topical administration of one or more active agents can include excipients such as talc, lactose and one or more silicic acids. Sprays can include a pharmaceutical propellant such as a fluorinated hydrocarbon propellant, carbon dioxide, or a suitable gas. Alternatively, a spray can be delivered from a pump-style spray device which does not require a propellant. A spray device delivers a metered dose of a composition contained therein, for example, using a valve for regulation of a delivered amount.

Opthalmic formulations of one or more active agents can include ingredients such as a preservative, a buffer and a thickening agent.

In particular embodiments of the present invention, an NGAL analog is an NGAL receptor agonist.

Further embodiments of the present invention include a method of treating acne in a subject which includes stimulating NGAL expression in a subject having acne. For example, NGAL expression is stimulated by administration of a transcription factor which upregulates transcription of a gene encoding NGAL and/or by administration of a nucleic acid encoding NGAL to the subject. Stimulators of NGAL expression illustratively include leukotriene B4 and cholesterol oleate. IL-17 or activators of NFκB is a further example of a stimulator of NGAL expression. Toll-like receptor 2 (TLR2) ligands and Toll-like receptor 3 (TLR3) ligands are stimulators of NGAL expression and one or more TLR ligands and/or one or more TLR3 ligands are administered to treat acne in a subject according to embodiments of the present invention.

Methods of inhibiting *Propionibacterium acnes* are provided by embodiments of the present invention which include administering NGAL, an NGAL analog, an NGAL stimulator or an analog of an NGAL stimulator to a subject colonized with *Propionibacterium acnes*. In particular embodiments of the present invention, administration includes contacting a *Propionibacterium acnes* bacterium with NGAL and/or a functional analog of NGAL. The skilled artisan will recognize that detecting *P. acnes* colonization in a subject and detecting *P. acnes* inhibition by methods and compositions according to the present invention can be achieved using well-known assay methods.

In preferred embodiments, the *Propionibacterium acnes* bacterium is in or on a human subject. The NGAL, an NGAL analog, an NGAL stimulator or an analog of an NGAL stimulator is administered to the human subject by a topical, local and/or systemic route. Methods of inhibiting *Propionibacterium acnes* in a subject are useful in treatment of conditions associated with *Propionibacterium acnes* colonization, such as acne and/or rosacea, for example.

In further embodiments of the present invention, methods of treating a retinoid-responsive condition in a subject are described which include administering a therapeutically effective amount of NGAL, an NGAL analog, an NGAL stimulator or an analog of an NGAL stimulator to a subject having a retinoid-responsive condition. Retinoid-responsive conditions illustratively include acne, rosacea, psoriasis, promyelocytic leukemia and neuroblastoma.

In addition to NGAL, methods and compositions of the present invention optionally include methods and compositions relating to genes described herein as regulated by isotretinoin, such as those listed in Tables II and III.

A method of treating a retinoid-responsive condition in a subject is provided according to embodiments of the present invention which includes administering a therapeutically effective amount of a Toll-like receptor 2 ligand to a subject having a retinoid-responsive condition.

In particular embodiments, the therapeutically effective amount of a Toll-like receptor 2 ligand is sufficient to increase NGAL and/or to increase IL-8 in the subject.

In particular embodiments, the retinoid-responsive condition is acne. Optionally, the Toll-like receptor 2 ligand is administered to an area of the skin of the subject affected by, or at risk of being affected by, acne.

Pam3CSK4, i.e. N-Palmitoyl-S-[2,3-bis(palmitoyloxy)-(2RS)-propyl]-[R]-cysteinyl-[S]-seryl-[S]-lysyl-[S]-lysyl-[S]-lysyl-[S]-lysine×3HCl, is an example of a TLR2 agonist included in embodiments of methods and compositions of the present invention.

A pharmaceutically acceptable carrier can be included in a composition including a Toll-like receptor 2 ligand.

The Toll-like receptor 2 ligand is formulated for topical, local and/or systemic administration to the subject according to particular embodiments of methods and compositions of the present invention.

A method of treating a retinoid-responsive condition in a subject is provided according to embodiments of the present invention which includes administering a therapeutically effective amount of a Toll-like receptor 3 ligand to a subject having a retinoid-responsive condition.

In particular embodiments, the therapeutically effective amount of a Toll-like receptor 3 ligand is sufficient to increase NGAL in the subject.

In particular embodiments, the retinoid-responsive condition is acne. Optionally, the Toll-like receptor 3 ligand is administered to an area of the skin of the subject affected by, or at risk of being affected by, acne.

Polyinosinic:polycytidylic acid (Poly I:C) is an example of a TLR3 agonist included in embodiments of methods and compositions of the present invention.

A pharmaceutically acceptable carrier can be included in a composition including a Toll-like receptor 3 ligand.

The Toll-like receptor 3 ligand is formulated for topical, local and/or systemic administration to the subject according to particular embodiments of methods and compositions of the present invention.

Methods of identifying NGAL analogs are provided by embodiments of the present invention which include administering a test compound to a cell sensitive to 13-cis retinoic acid-induced apoptosis to produce a treated cell and assaying the treated cell for a marker of apoptosis and/or endogenous production of NGAL. A test compound which is a functional analog of NGAL is ineffective to induce the marker of apoptosis in absence of a functional NGAL receptor in the treated cell in particular embodiments of inventive methods.

Embodiments of inventive compositions and methods are illustrated in the following examples. These examples are provided for illustrative purposes and are not considered limitations on the scope of inventive compositions and methods.

EXAMPLES

Example 1

Patient Selection and Tissue Biopsies

Patients were recruited to have skin biopsies of their upper backs at baseline and after one week of treatment with 13-cis RA. A total of 7 patients that were prescribed isotretinoin by their dermatologist for their severe acne were enrolled in the study after signing informed consent forms. Information regarding patient age, sex, the time of biopsy, and the dose of isotretinoin that patients were receiving at the time of their second biopsy are presented in Table I.

TABLE I

Isotretinoin Patient Demographic

Patient Demographics

| Subject # | Age | Sex | Dose mg/kg/d | Biopsy (days) |
|---|---|---|---|---|
| 1 | 15 | M | 0.5 | 7 |
| 2 | 17 | M | 0.5 | 7 |
| 3 | 17 | M | 0.5 | 7 |
| 4 | 21 | F | 0.67 | 7 |
| 5 | 17 | M | 0.67 | 7 |
| 6 | 20 | F | 0.67 | 7 |
| 7 | 23 | M | 0.5 | 7 |
| Mean ± SD | 18.5 ± 2.8 | | 0.57 ± 0.09 | 7 ± 0 |

All protocols were approved by the Institutional Review Board of The Pennsylvania State University College of Medicine and were conducted according to the principles outlined in the Declaration of Helsinki. All subjects gave informed consent. Subjects included males and females ages 14 to 40 years who were scheduled by their dermatologist to receive treatment with 13-cis RA (isotretinoin, brand not noted) for severe acne. All aspects of the patients' treatment with 13-cis RA apart from the skin biopsies were standard of care and were not part of this research. Exclusion criteria included patients with underlying medical conditions requiring treatment with systemic medications that might interfere with the gene array analysis.

Seven patients had 5-mm punch biopsies of skin from the upper back taken at baseline and again at day 7 of treatment. Biopsies were taken from non-inflamed skin in areas apart from acne lesions. Biopsies were placed on ice and immediately transferred to the laboratory where they were trimmed of fat and a small section of each biopsy was taken and paraffin-embedded for histology and immunohistochemistry. The remaining portion of the biopsy was flash frozen in liquid nitrogen and used for total RNA isolation.

Example 2

Histology suggests decrease in sebaceous gland volume after one week of 13-cis RA treatment.

Hematoxylin and eosin staining was performed on sections of patient skin obtained from biopsies of skin from the upper back taken at baseline and at one week of treatment. A total of 17 sections at baseline and 19 sections at one week taken from 6 patients were analyzed using image analysis software.

Images were captured using a Spot digital camera (Diagnostic Instruments, Inc.) and measurements were obtained with Image Pro Plus Imaging Software version 3.0 after spatial calibration with a micrometer slide under the 10× objective. All areas of the sebaceous gland were circled using a free-hand measuring tool and the total area of the sebaceous gland was calculated in each section from the baseline and the one-week biopsies. The average area for each distinct sebaceous gland was calculated from sections analyzed. An ANOVA Single Factor statistical test ($\alpha=0.05$) was performed to look for significant differences in sebaceous gland area before and after one week of treatment.

At baseline, sebaceous glands were characteristically large and multi-lobular. Although changes in architecture were not obvious at one week of isotretinoin treatment, an early decrease in the overall size of the sebaceous glands was suggested. The mean area of sebaceous glands in the baseline samples was $0.23\pm0.09$ mm$^2$ (mean±SEM) compared to $0.12\pm0.02$ mm$^2$ in the one week samples, which was not significant using a paired t-test ($p=0.16$) (data not shown).

Example 3

13-cis RA Induces Apoptosis in Patient's Sebaceous Glands at One Week

Skin sections were obtained from paraffin blocks of 7 patients sampled at baseline and one week of isotretinoin. A TUNEL-peroxidase assay followed by counter staining with hematoxylin was performed on skin biopsies obtained from patients at baseline and at one week of 13-cis RA therapy (n=6 pairs of samples).

In this procedure sections of baseline and post-treatment biopsies from 7 patients were subjected to deparaffinization, rehydration and permeabilization with 0.1% Triton-X, 0.1% sodium citrate in phosphate buffered saline. Sections were subjected to In Situ Cell Death Detection, Peroxidase kit (Roche Diagnostics, Indianapolis, Ind.) followed by counter staining with hematoxylin. DNase I treatment of positive and negative controls (without terminal transferase) were included as assay controls according to manufacturer's instructions. At least 2 baseline and one week skin sections were analyzed from every patient. Patient 7 was omitted from the analysis as no sebaceous glands were found in baseline biopsy sections. Results were quantified by counting positive stained cells/total cells in sebaceous glands. Data represents mean±SD, n=6 patients; paired t-test was used for statistical analysis and considered significant if p<0.05.

A 4-fold increase in the percentage of TUNEL positive cells was noted within the sebaceous gland at one week of therapy compared to baseline (45.9±11.9% vs. 13.9±6% TUNEL positive cells, p=0.005, paired t-test, $\alpha=0.05$). FIG. 1 shows representative sections from Patient 4 taken at baseline and at one week of isotretinoin treatment. NC=negative control which consists of sections from a skin specimen treated with DNase I and processed without terminal transferase enzyme. PC=positive control which consists of sections from a skin specimen treated with DNase I and subjected to the full TUNEL assay. Total magnification 400×.

TUNEL staining was strongest in the nuclei of sebocytes in the basal layer of the sebaceous gland and in early differentiated sebocytes adjacent to the basal layer, arrows. Apoptosis was selective for the sebaceous gland as no apoptosis was detected within the epidermis.

Example 4

Gene array expression analysis was performed on patient skin biopsies at baseline and one week of isotretinoin therapy. Gene expression analysis of skin from patients treated with 13-cis RA revealed significant increases in genes encoding calcium binding proteins, retinoid signaling molecules, solute carriers and serine proteases.

In this procedure, total RNA was isolated from skin biopsies and DNase treated using the RNeasy Fibrous Tissue Kit (Qiagen Inc., Valencia, Calif.). Approximately 2 μg of total RNA from each sample was used to generate double stranded cDNA using a T7-oligo (dT) primer. Biotinylated cRNA, produced through in vitro transcription, was fragmented and hybridized to an Affymetrix human U133A 2.0 microarray for one week biopsies. The arrays were processed on a GeneChip Fluidics Station 450 and scanned on an Affymetrix GeneChip Scanner (Santa Clara, Calif.). Expression signals were normalized as previously described (47, 60, 61). Significant gene expression alterations were identified using Significance Analysis of Microarrays (SAM) computer software (62). SAM controls the false positives resulting from multiple comparisons through controlling the false discovery rate (FDR) (63). FUR is defined as the proportion of false positive genes among all genes that are considered significant. The results of these array analyses have been submitted to the National Center for Biotechnology Information Gene Expression Omnibus database under the accession number GSE10434. This is considered a super series and contains both the 1 week patient data and the cell culture model (SEB-1) data, described below. For the 1 week data alone the accession number is GSE10432. For the SEB-1 data alone: GSE10433.

Array data was not generated for patient 3 due to insufficient quantity of RNA. Using a false discovery rate (FDR) of 0.05 that corresponds to a 5% chance of false positive gene changes, 38 genes were significantly up-regulated and 5 genes were significantly down-regulated by 13-cis RA when compared to baseline. (Table II; and Tables V and VI for a full listing of significantly changed genes). LCN2 was among the most highly up-regulated genes.

TABLE II

Significantly changed genes in patient skin after 1 week of isotretinoin therapy

| Fold Change | Gene Title | Gene Symbol |
|---|---|---|
| 7.03 | lipocalin 2 (oncogene 24p3) | LCN2 |
| 6.2 | S100 calcium binding protein A7 (psoriasin 1) | S100A7 |
| 4.53 | S100 calcium binding protein A9 (calgranulin B) | S100A9 |
| 3.78 | solute carrier family 12 (K/Cl transporters) | SLC12A8 |
| 3.32 | cytochrome P450, family 2, subfamily B | CYP2B7P1 |
| 2.61 | serine (or cysteine) proteinase inhibitor | SERPINA3 |
| 2.61 | retinoic acid receptor responder (TIG 1) | RARRES1 |
| 2.35 | transmembrane protease, serine 4 | TMPRSS4 |
| 1.99 | S100 calcium binding protein P | S100P |
| 1.92 | ATPase, H+/K+ transporting, nongastric, alpha | ATP12A |
| 1.91 | chemokine (C-C motif) ligand 2 | CCL2 |
| 1.81 | retinol binding protein 1, cellular | RBP1 |
| 1.69 | solute carrier family 6 (amino acid transporter) | SLC6A14 |
| 1.67 | E74-like factor 3 (ets domain transcription factor) | ELF3 |
| 1.56 | cellular retinoic acid binding protein 2 | CRABP2 |
| 1.52 | defensin, beta 1** | DEFB1 |
| 1.51 | calbindin 2, 29 kDa (calretinin) | CALB2 |

TABLE II-continued

Significantly changed genes in patient skin after 1 week of isotretinoin therapy

| Fold Change | Gene Title | Gene Symbol |
|---|---|---|
| 1.5 | S100 calcium binding protein A2 | S100A2 |
| 1.49 | involucrin | IVL |
| 1.49 | interleukin 27 receptor, alpha | IL27RA |
| −2.29 | solute carrier family 26, member 3 | SLC26A3 |
| −2.27 | phospholipase A2, group VII (PAF acetylhydrolase) | PLA2G7 |
| −2.13 | phosphodiesterase 6A, cGMP-specific, rod, alpha | PDE6A |

Example 5

Gene expression in SEB-1 sebocytes treated with 13-cis RA is similar to profile the observed in human skin.

To identify sebocyte-specific gene changes induced by 13-cis RA, array analysis was performed in SEB-1 sebocytes on three samples treated with 0.1 micromolar 13-cis RA and three samples treated with vehicle.

The SEB-1 human sebocyte cell line was generated by transfection of secondary sebocytes with SV40 Large T antigen and was cultured in standard culture medium as previously described (59). 13-cis RA (R 3255) was purchased through SIGMA (St. Louis, Mo.). 10 mM Stock solutions of 13-cis RA dissolved in ethanol were handled under dimmed yellow light and stored under $N_2$ gas at −20° C. until use. Purified recombinant human NGA-L protein (amino acids 21-198) was purchased from R&D Systems (Minneapolis, Minn.) ready-to-use and was stored at −20° C. until needed. Stock solutions were diluted to desired concentrations in standard sebocyte culture medium.

Total RNA was isolated from SEB-1 sebocytes treated with 0.1 μM 13-cis RA or vehicle alone (0.001% ethanol) in three independent samples using the RNeasy kit (Qiagen Inc., Valencia, Calif.). Approximately 2 μg of total RNA from each sample was used to generate double stranded cDNA using a T7-oligo (dT) primer. Biotinylated cRNA, produced through in vitro transcription, was fragmented and hybridized to an U95Av2 microarray for SEB-1 sebocytes. The arrays were processed on a GeneChip Fluidics Station 450 and scanned on an Affymetrix GeneChip Scanner (Santa Clara. Calif.). Expression signals were normalized as previously described (47, 60, 61). Significant gene expression alterations were identified using Significance Analysis of Microarrays (SAM) computer software (62). SAM controls the false positives resulting from multiple comparisons through controlling the false discovery rate (FUR) (63). FDR is defined as the proportion of false positive genes among all genes that are considered significant.

A total of 85 genes (78 different genes) were significantly influenced by 13-cis RA: 58 were upregulated and 27 were down-regulated. Select genes whose expression was significantly changed genes are listed in Table III. (See Tables V and VI for the full listing of significantly changed genes.) As in the patient samples, LCN2 and the tumor suppressor, TIG1, demonstrated the greatest changes in gene expression.

TABLE III

Selected significantly changed gene in SEB-1 sebocytes after 13-cis RA treatment

| Fold Change | Gene Title | Gene Symbol |
|---|---|---|
| 12.25 | retinoic acid receptor responder (tazarotene induced) 1 | RARRES1 |
| 7.04 | lipocalin 2 (oncogene 24p3) | LCN2 |
| 5.95 | tumor necrosis factor, alpha-induced protein 2 | TNFAIP2 |
| 5.91 | hydroxyprostaglandin dehydrogenase 15-(NAD) | HPGD |
| 4.64 | cytochrome P450, family 1, subfamily B, polypeptide 1 | CYP1B1 |
| 4.18 | tumor necrosis factor (ligand) superfamily, member 10 | TNFSF10 |
| 3.70 | serine (or cysteine) proteinase inhibitor, | SERPINB3 |
| 3.65 | homeo box A5 | HOXA5 |
| 3.43 | insulin-like growth factor binding protein 3 | IGFBP3 |
| 3.29 | aldehyde dehydrogenase 1 family, member A3 | ALDH1A3 |
| 3.22 | retinoic acid receptor responder (tazarotene induced) 3 | RARRES3 |
| 3.08 | oxidised low density lipoprotein (lectin-like) receptor 1 | OLR1 |
| 2.60 | cyclin-dependent kinase inhibitor 1A (p21, Cip1) | CDKN1A |
| 2.51 | E74-like factor 3 (ets domain transcription factor, epithelial-specific) | ELF3 |
| 2.42 | interferon regulatory factor 1 | IRF1 |
| 2.42 | interferon-induced protein with tetratricopeptide repeats 3 | IFIT3 |
| 2.09 | proteasome (prosome, macropain) subunit, beta type, 10 | PSMB10 |
| 2.08 | vascular cell adhesion molecule 1 | VCAM1 |
| 2.07 | annexin A9 | ANXA9 |
| 2.07 | 2',5'-oligoadenylate synthetase 1, 40/46 kDa | OAS1 |
| 1.85 | GATA binding protein 3 | GATA3 |
| 1.79 | protein kinase C, alpha | PRKCA |
| 1.70 | nuclear factor of kappa light polypeptide gene enhancer in B-cells | NFKB2 |
| 1.69 | Fas (TNF receptor superfamily, member 6) | FAS |
| −4.68 | keratin 6A /// keratin 6C | KRT6A |
| −3.94 | FK506 binding protein 5 | FKBP5 |
| −3.25 | ELOVL family member 5, elongation of long chain fattyacids | ELOVL5 |

Example 6

QPCR Verification of Select Genes from Array Analyses

QPCR analyses showed that the direction and magnitude of the change in expression for the selected genes were similar to those observed with the gene array analyses and verified siRNA knockdown and immunoblotting experiments.

Applied Biosystems' Assays-on-Demand Taqman Universal PCR Master Mix, primer/probe sets, and ABI's 7900HT Fast Real-Time PCR System with 384-well plate block module were used according to manufacturer's instructions (Applied Biosystems, Foster City, Calif.). Integrity of isolated RNA was verified by agarose gel electrophoresis. cDNA was generated from 1 µg of total RNA, primed with oligo-dT, using the Superscript First-Strand Synthesis System for RT-PCR (Invitrogen, Carlsbad, Calif.). Diluted cDNA from the one week samples were run for the reference gene TATA binding protein (TBP) and genes of interest: lipocalin 2, (LCN2) RARRES1, S100A7, SERPINA3 and PLA2G7. For gene array verification, 8 independent samples of SEB-1 sebocytes treated with 0.1 µM 13-cis RA or vehicle alone for 72 hours were analyzed. Genes of interest included: LCN2, RARRES1, insulin-like growth factor binding protein 3 (IGFBP-3), GATA3, ZBTB16 and potential LCN2 cell surface receptor (SLC22A17). Expression of TBP, GAPDH and LCN2 was analyzed in 6 independent SEB-1 samples for the siRNA knockdown experiments. SEB-1 sebocytes treated with increasing concentrations of ATRA (n=5) were analyzed for the reference gene, TBP, and LCN2. In all experiments, assay controls included samples omitting reverse transcriptase enzyme as well as samples without cDNA. Data was analyzed using the Relative Expression Software Tool (REST-XL version 1) software program (64) with efficiency correction and a p-value <0.05 was considered significant.

Figure 2:
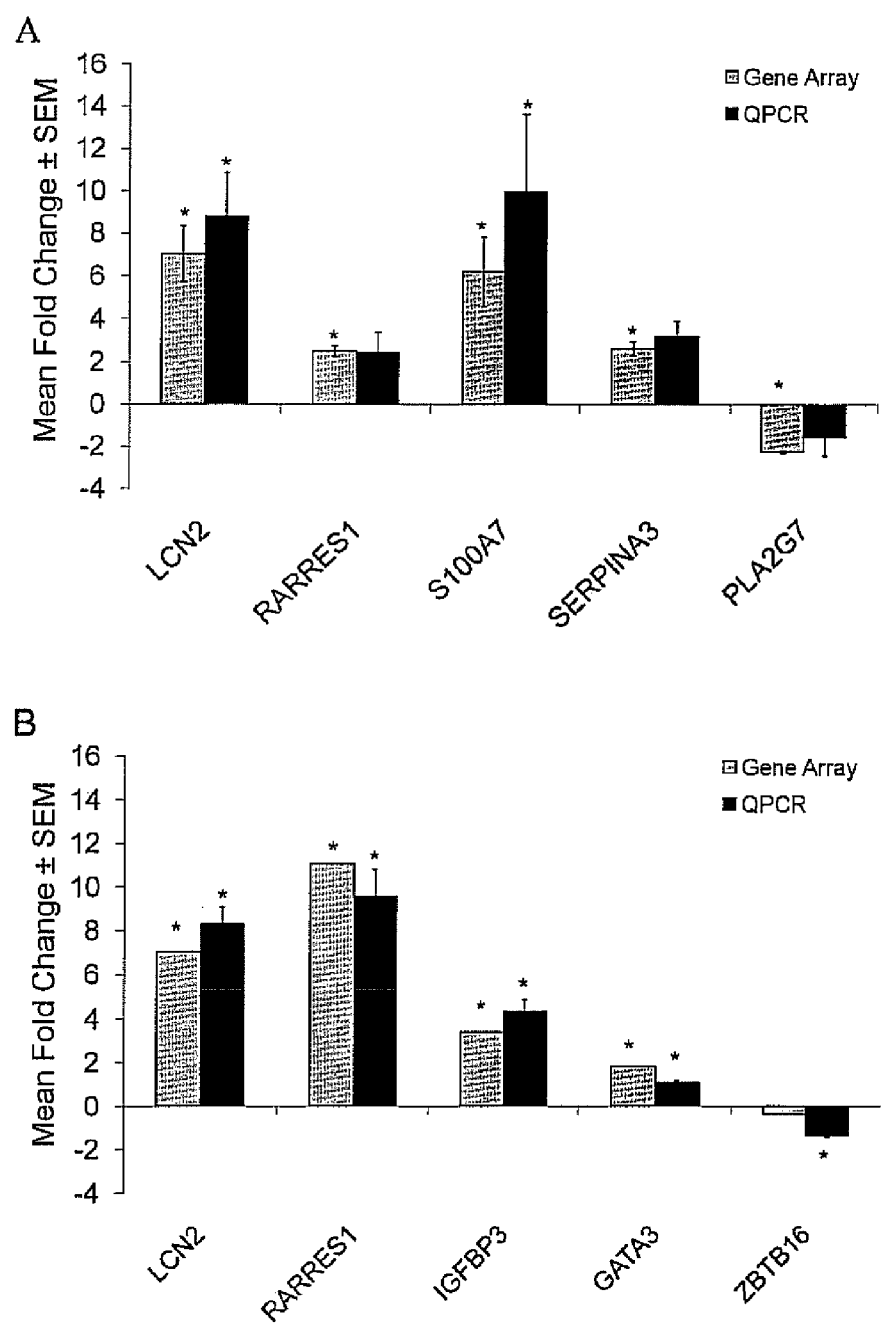
FIG. 2A is a graph showing comparison of array analysis and QPCR on RNA obtained from patient skin biopsies at baseline and one week of 13-cis RA treatment.
FIG. 2B is a graph showing comparison of array analysis and QPCR on RNA obtained from SEB-1 sebocytes incubated for 72 hours.

Sufficient RNA was available from 5 of 7 patients (all but Patients 3 and 4) to verify gene expression changes by QPCR for LCN2, retinoic acid receptor responder 1 (RARRES1, TIG1), psoriasin (S100A7), serine protease inhibitor A3 (SERPINA3) and phospholipase A2 group 7 (platelet activating factor acetyl hydrolase, PLA2G7). FIG. 2A shows comparison of array analysis and QPCR on RNA obtained from patient skin biopsies at baseline and one week of 13-cis RA treatment. Data represent the mean±SEM of the fold-change in gene expression as determined by QPCR in 5 subjects compared to array analysis performed in 6 subjects.

For SEB-1 sebocytes, gene array expression changes were verified by QPCR for LCN2, TIG1, insulin-like growth factor binding protein 3 (IGFBP3), GATA transcription factor 3 (GATA3) and ZBTB16; zinc finger and BTB domain-containing 16. FIG. 2B shows comparison of array analysis and QPCR on RNA obtained from SEB-1 sebocytes incubated for 72 hours in the presence or absence of 13-cis RA. Data represent the mean±SEM of the fold change in gene expression as determined by QPCR in 8 samples compared to array analysis performed in 3 samples. QPCR results were analyzed by REST-XL software program and *p<0.05 was considered significant.

Example 7

13-cis RA Induces Expression of Neutrophil Gelatinase Associated Lipocalin (NGAL) in Patients' Sebaceous Glands Patient skin biopsies that were taken at baseline and at one week of isotretinoin therapy were used to assess NGAL expression and localization using immunohistochemistry.

Figure 3:
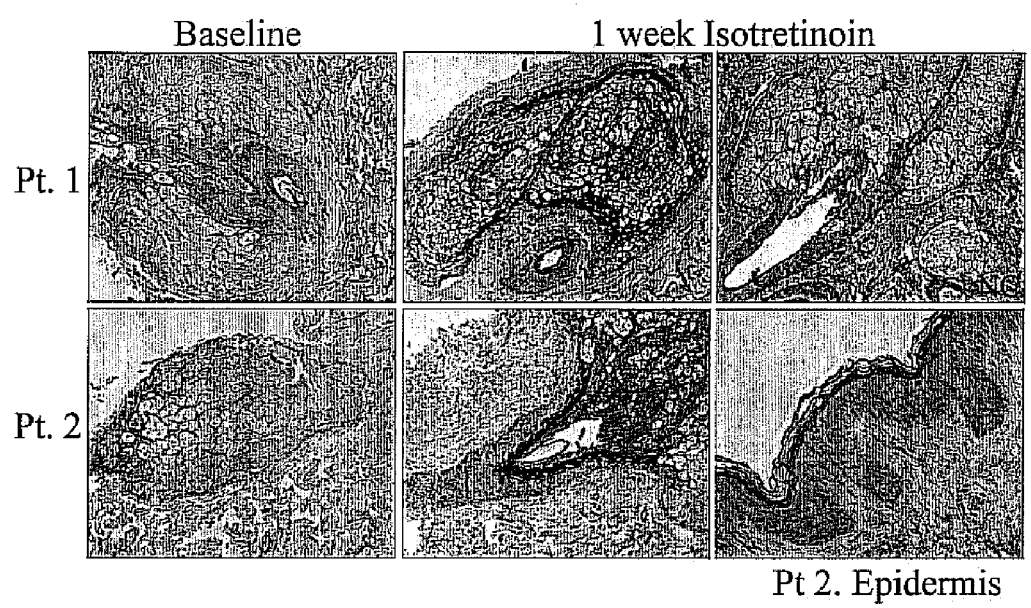
FIG. 3 is a reproduction of images showing immunostained sections indicating that NGAL (also termed lipocalin 2 and LCN2) expression is increased in sebaceous glands in patients biopsied at one week of isotretinoin treatment.

FIG. 3 shows that NGAL expression is increased in sebaceous glands in patients biopsied at one week of isotretinoin treatment. Immunohistochemistry using an antibody to NGAL was performed on skin sections taken at baseline and at one week of isotretinoin treatment. Sections were incubated overnight with a 1:50 dilution of mouse monoclonal lipocalin 2/NGAL antibody and developed using AEC chromagen (dark areas). All sections were counterstained with hematoxylin. Representative images at baseline and after 1 week isotretinoin from Patients 1 and 2 are shown. An image of the epidermis after isotretinoin treatment from Patient 2 is shown. NC-negative control, consists of a normal human skin incubated with normal mouse $IgG_1$ antibody. Original magnification: 100×. NGAL was expressed in the sebaceous gland and duct of samples of skin taken at one week of isotretinoin therapy. NGAL was not expressed in the epidermis.

In each patient, NGAL expression was detected specifically within the basal layer of the sebaceous gland and upper sebaceous duct in sections from skin taken at one week of therapy as shown in FIG. 3. NGAL expression was not noted within the epidermis. This pattern of NGAL expression is comparable to the pattern of TUNEL positive cells after isotretinoin treatment. NGAL immunoreactivity and TUNEL positive cells are both present within the basal layer of the sebaceous gland and are absent from the epidermis.

In general, NGAL expression is increased after one week of isotretinoin treatment although, the amount of increase varied among the patients as shown in Table IV. Patient 7 was omitted from the analysis because no sebaceous glands were captured in the baseline biopsy sections. In 2 out of the 6 patients (Patients 4 and 6, the only females in the study), a minimal increase in NGAL staining was noted. Of the 6 patients examined, only one had NGAL expression in sebaceous glands at baseline, see Table IV.

TABLE IV

Quantification of NGAL staining for individual patients at baseline and after one week isotretinoin therapy.

| Patient | Baseline (% of sebaceous gland positive for NGAL) | 1-week (% of sebaceous gland positive for NGAL) |
|---|---|---|
| 1 | 0.0 | 36.7 |
| 2 | 0.0 | 11.3 |
| 3 | 0.0 | 27.1 |
| 4 | 0.0 | 1.1 |
| 5 | 11.1 | 12.1 |
| 6 | 0.0 | 1.0 |
| Average | 1.9 | 14.9 |
| SEM | 1.9 | 5.9 |

Example 8

The expression of NGAL within SEB-1 sebocytes was verified by QPCR and western blotting showing that 13-cis RA and ATRA increase LCN2 mRNA and NGAL protein expression in SEB-1 sebocytes.

LCN2 mRNA expression was verified by QPCR after 48 hours of retinoid treatment. Data represent mean±SEM of the fold-change in gene expression as determined by QPCR of 5 independent samples. Statistical analysis was performed with REST-XL software program and considered significant if *p<0.05.

For Western blotting, mouse monoclonal antibody to lipocalin 2 (NGAL) was obtained from Abcam, Inc., (Cambridge, Mass.). The 24p3R(NGAL receptor) affinity purified antibody, positive (HEK 293 cell lysate) and negative (T47D cell lysate) controls were kindly provided by Dr. Michael Green (University of Massachusetts Medical School). GAPDH (#2118), Cleaved caspase 3 (#9664), β-actin (#4967) and anti-rabbit horseradish peroxidase (HRP) linked secondary antibodies (#7074) were purchased from Cell Signaling Technology (Beverly, Mass.). Secondary Anti-mouse HRP antibody was purchased from Santa Cruz Biotechnology Inc. (Santa Cruz, Calif.).

SEB-1 sebocytes (passages 22-28) were in standard culture medium until 50-75% confluent. Treatments of 13-cis RA (0.1 nM, 1 nM, 10 nM, 0.1 μM, or 1 μM) or ethanol vehicle (0.01% or less) were applied for 48 or 72 hours. In parallel studies, identical concentrations of all-trans retinoic acid (ATRA) were applied for 72 hours. In all experiments, each plate was considered an independent sample and total protein was collected. Blots were incubated with appropriate primary and secondary antibodies followed by densitometry. Each experiment was repeated a minimum of 3 independent times. Data was analyzed using a paired t-test and results were considered significant if $p<0.05$.

Figure 4:
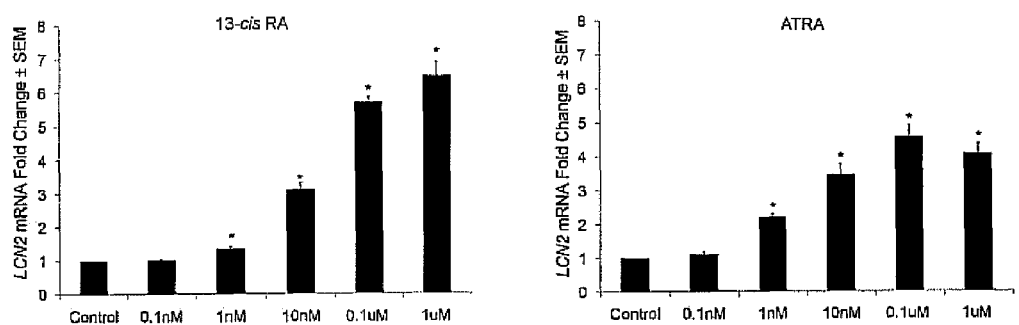
FIG. 4A is a set of two graphs showing expression of LCN2 mRNA detected after 48 hours of 13-cis RA (left panel) or ATRA (right panel) treatment.
FIG. 4B is a set of two graphs and corresponding immunoblots showing LCN2 protein expression after 72 hours of 13-cis RA (left panel) or ATRA (right panel) treatment.
Figure 4:
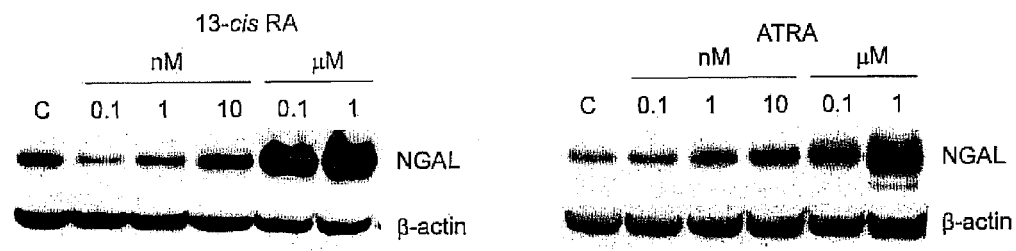
Figure 4:
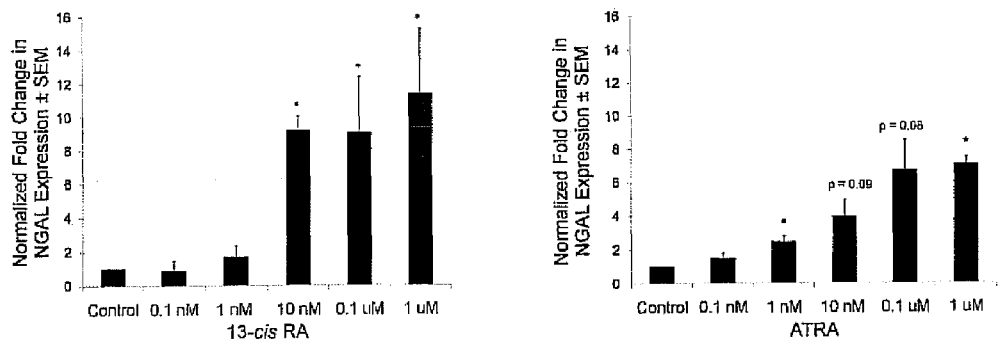

As shown in FIG. 4A, expression of LCN2 mRNA was detected after 48 hours of 13-cis RA treatment. 13-cis RA concentrations of 1 nM and greater significantly increased LCN2 mRNA levels to approximately 6-fold with micromolar concentrations when compared to control.

Protein expression was verified by western blot at 72 hours of retinoid treatment. Blots were incubated with primary antibody to NGAL as well as β-actin as a loading control. Blots were analyzed by densitometry and normalized to β-actin. The graph represents normalized fold-change values (mean±SEM) relative to control for a minimum of 3 independent blots. Statistical analysis was performed with paired t-test, *$p<0.05$. As shown in FIG. 4B, after 72 hours of treatment with concentrations ranging from 0.1 nM to 1 μM 13-cis RA, NGAL protein expression increased in a dose-dependent manner to a maximum of approximately 10-fold with micromolar concentrations in SEB-1 sebocytes when compared to control ($p<0.05$).

The first 1000 base pairs of the LCN2 promoter were scanned for retinoic acid response elements (RAREs) using the predefined consensus sequences within the Transfac database through the Transcription Element Search System (TESS) and reveals the presence of both RAR and RXR binding sites. Prior studies suggest that 13-cis RA acts as a reservoir of ATRA and that after isomerization to ATRA, acts via binding nuclear retinoic acid receptors (12). Although, in other studies, retinoid receptor-independent modulation of signaling pathways by ATRA, such as binding to PKC, have also been reported (13, 14).

To address this issue, SEB-1 sebocytes were treated with increasing concentrations of ATRA in parallel studies and examined for expression of LCN2 mRNA and NGAL protein. QPCR and immunoblotting show that NGAL expression also increased in a dose-dependent manner with ATRA when compared to control. The level of NGAL expression induced by ATRA is less than that with 13-cis RA (7-fold vs. 10-fold) but the difference between ATRA and 13-cis RA was not significant, see FIGS. 4A and 4B.

Example 9

Recombinant NGAL Protein Induces Apoptosis in SEB-1 Sebocytes

SEB-1 sebocytes were treated with increasing concentrations of purified recombinant human NGAL (rhNGAL) protein and a TUNEL assay was performed.

For the TUNEL assay, SEB-1 sebocytes (passage 22-28) were cultured in 12-well plates in standard medium until approximately 30-40% confluent. Wells were rinsed with phosphate buffered saline (PBS) and treated in duplicate with vehicle control, 1 pg/mL, 10 pg/mL, 100 pg/mL, 1 ng/mL, or 10 ng/mL of recombinant human NGAL (R&D Systems, Minneapolis, Minn.) or human actin (negative control; Cytoskeleton, Denver, Colo.) protein for 24 hours. In all experiments, each well was considered one sample Samples were prepared by manufacturer's instructions for In Situ Cell Death Detection Kit, Fluorescein (Roche Diagnostics, Indianapolis. Ind. DNase I treatment of positive and negative controls (without terminal transferase) were included as assay controls according to manufacturer's instructions. Results were analyzed and quantified by counting positive stained cells per total number of cells in 3 representative fields per well for each of the treatments done in duplicate. Four independent rhNGAL experiments were performed whereas treatment with actin was performed once. Statistical analyses were performed between control and each treatment concentration using ANOVA Two Factor with Replication and considered significant if $p<0.05$.

As noted above, SEB-1 sebocytes were treated with vehicle as a control, 1 pg/mL, 10 pg/mL, 100 pg/mL, 1 ng/mL or 10 ng/mL of purified recombinant human NGAL protein (R&D Systems) or the same concentrations of human actin protein for 24 hours. After 24 hours of treatment with NGAL, the percentage of TUNEL positive cells in SEB-1 sebocytes was significantly increased to a maximum of approximately 35% using 1 ng/mL rhNGAL as shown in FIGS. 5A and 5B.

Figure 5:
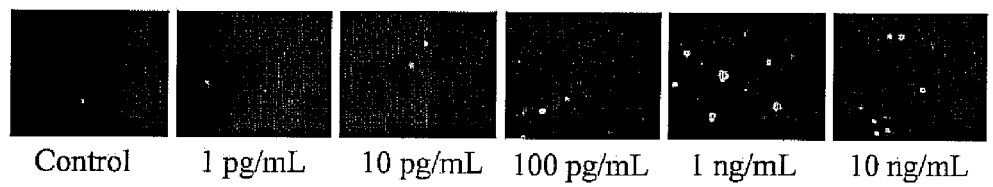
FIG. 5A shows representative images of TUNEL assay results following treatment of SEB-1 sebocytes using purified recombinant human NGAL at various concentrations and indicating increasing apoptosis with increasing dosage.
FIG. 5B is a graph showing quantification of the percentage of TUNEL positive stained SEB-1 sebocytes in each treatment group after 24 hours of treatment with purified recombinant human NGAL at various concentrations.
Figure 5:
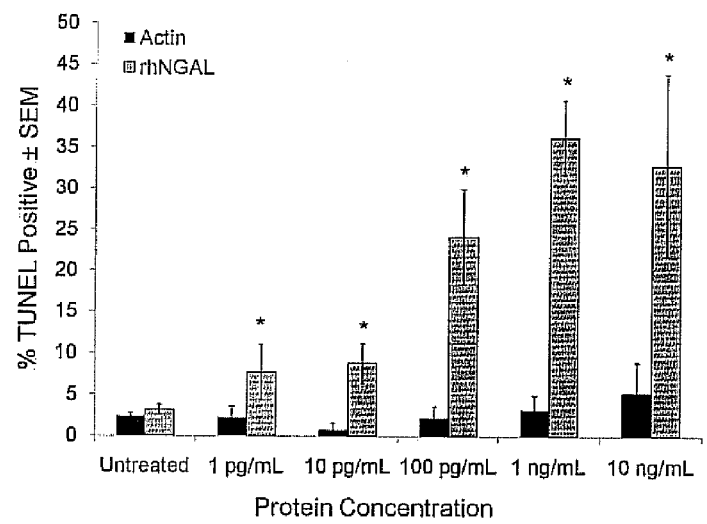

FIG. 5A shows representative images of the TUNEL assay using rhNGAL are shown. Original magnification: 200×. FIG. 5B shows quantification of the percentage of TUNEL positive stained cells per treatment at 24 hours. Data represent mean±SEM, n=4-8. Parallel experiments to control for non-specific effects of protein were performed using human actin protein (n=2). The percentage of TUNEL positive cells is less than 5% with all concentrations of actin, which is similar to control values. Statistical analyses were performed between vehicle control and each treatment concentration of rhNGAL using ANOVA Two Factor with Replication; * $p<0.05$. rhNGAL significantly increased TUNEL staining compared to control over a wide range of concentrations with maximal induction noted at 1 ng/mL.

Example 10

NGAL Mediates 13-cis RA-Induced Apoptosis in Human Sebocytes

To test the hypothesis that NGAL mediates the apoptotic effect of 13-cis RA on sebcoytes, siRNA to LCN2 is utilized in the presence of 13-cis RA and the effect on apoptosis using western blotting for cleaved caspase 3, the activated form of caspase 3 is examined.

Optimization of the appropriate nucleofection solution and program was carried out according to manufacturer's instructions using the Cell Line Optimization Nucleofector Kit with 2 μg of pgmaxGFP DNA in combination with the highest efficiency (GFP expression) and lowest mortality. Program T-20 with solution T was chosen for future experiments. Efficiency of nucleofection was determined by GFP expression quantified by flow cytometry with mock-nucleofected SEB-1 sebocyte controls. Very high levels of GFP expression (87%, 90%, 73%, and 57%) were detected at 24, 48, 72 and 96 hours post-nucleofection, respectively.

Using ON-TARGETplus Smartpool Human LCN2, Human GAPDH and siCONTROL siRNA duplex oligonucleotides (Dharmacon Research, Lafayette, Colo.), nucleofection was performed as suggested by Dharmacon and Amaxa Biosystems. SEB-1 sebocytes, $2 \times 10^6$ cells per 100 microliter reaction were nucleofected with 1 μg siCON- TROL, GAPDH or LCN2 siRNA. 13-cis RA (0.1 µM) was added 24 hours post-nucleofection. Extent of siRNA knockdown of gene expression was verified by QPCR and western blotting for LCN2/NGAL and GAPDH at various time points after 13-cis RA treatment. Involvement of LCN2/NGAL in mediating 13-cis RA induced apoptosis was assessed by cleaved caspase 3 protein expression using western blotting.

QPCR results shows in FIG. 6A demonstrate that the expression of LCN2 mRNA was successfully decreased 15-fold (93%) by the siRNA compared to siCONTROL in SEB-1 cells that were treated for 48 hours with 13-cis RA. FIG. 6A shows QPCR analysis of LCN2 and GAPDH mRNA levels at 48 hours of 0.1 µM 13-cis RA treatment. The expression of LCN2 mRNA was successfully decreased 15-fold by the LCN2 siRNA compared to siCONTROL whereas expression of GAPDH was minimally affected by siRNA to LCN2. GAPDH mRNA expression was decreased 4-fold by the specific GAPDH siRNA when compared to siCONTROL whereas siRNA to GAPDH had minimal effects on expression of mRNA for LCN2. Data represent mean±SEM; n=6. * $p<0.05$ as determined by REST-XL program. As a control, the specificity of siRNA knockdown was verified using siRNA to GAPDH in parallel samples. GAPDH and LCN2 gene expression were successfully inhibited in their respective samples.

FIG. 6B shows that protein levels of NGAL were undetectable by western blotting after 48 and 72 hours of 13-cis RA treatment. FIG. 6B displays immunoblot analysis of GAPDH and NGAL protein levels: NGAL protein expression is decreased to undetectable levels by western blotting at 48 and 72 hours of 0.1 µM 13-cis RA treatment with LCN2 siRNA. Representative blots of 4 independent experiments are shown.

After confirming successful inhibition of LCN2 and NGAL expression by siRNA, the effect of LCN2 on apoptosis was determined.

Figure 6:
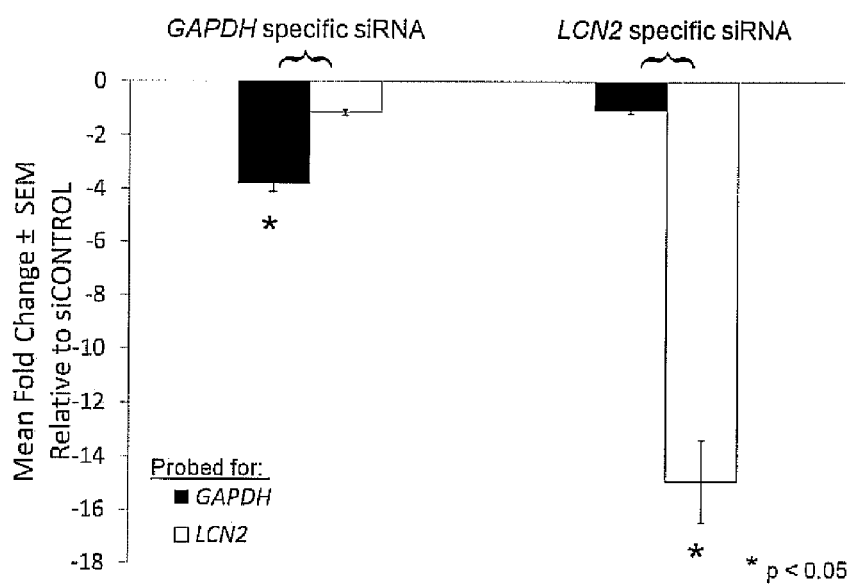
FIG. 6A is a graph showing QPCR results demonstrating decreased expression of LCN2 mRNA following treatment of SEB-1 sebocytes with anti-LCN2 siRNA.
FIG. 6B is a reproduction of images of immunoblots showing that protein levels of NGAL were undetectable by western blotting after 48 and 72 hours of 13-cis RA and anti-LCN2 siRNA treatment.
Figure 6:
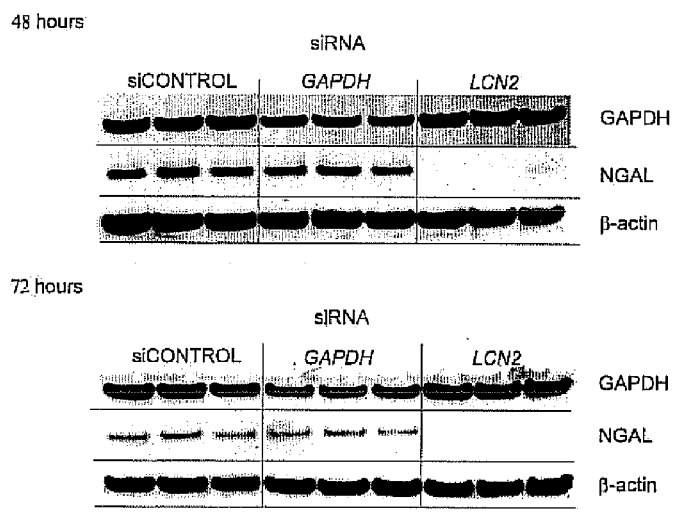
Figure 7:
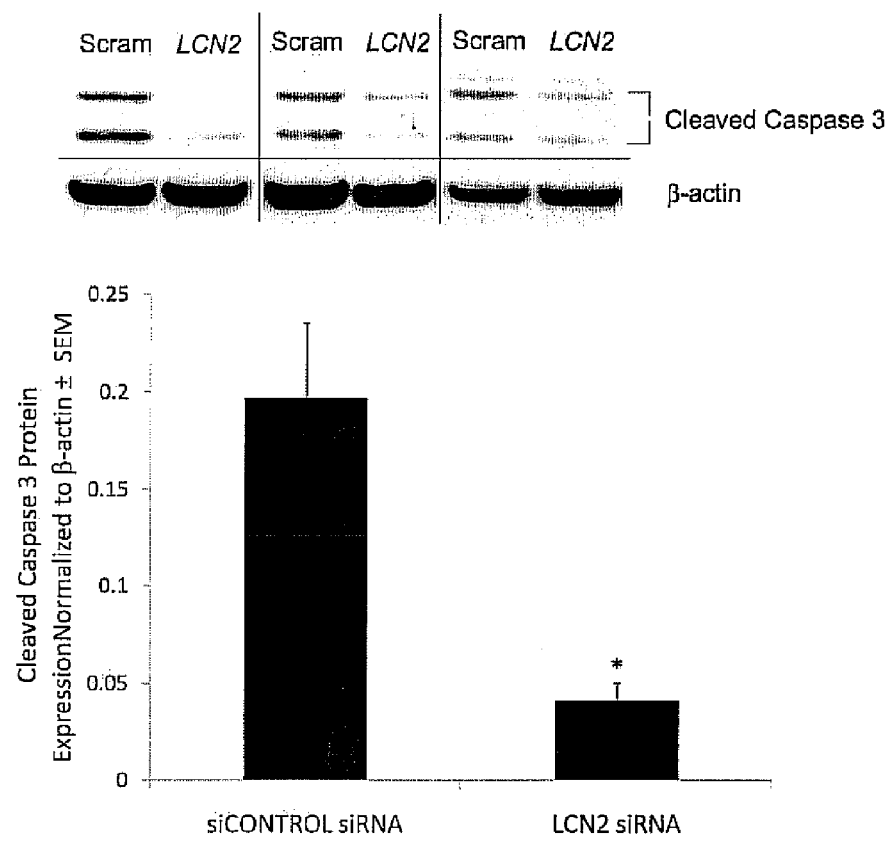
FIG. 7 is an immunoblot and corresponding graph showing that treatment of cells with anti-LCN2 siRNA blocks the induction of caspase 3 cleavage by 13-cis retinoic acid in SEB-1 sebocytes.

Under siRNA conditions described for FIG. 6, immunoblotting revealed that siRNA to LCN2 decreases expression of cleaved caspase 3 by approximately 5-fold compared to siRNA control. siRNA to LCN2 in the presence of 13-cis RA decreased expression of cleaved caspase 3 to approximately 20% of control levels, corresponding to a 5-fold reduction, as indicated in FIG. 7.

Blots in FIG. 7 were incubated with primary antibodies to cleaved caspase 3 as well as β-actin as a loading control to normalize densitometry values. Three independent "scrambled siCONTROL (SCRAM)" and "LCN2" western blots are shown. p17 and p19 are the cleaved or "active" fragments of caspase 3. The graph in FIG. 7 represents the normalized expression of cleaved caspase 3 from 5 independent western blots; statistical analysis was performed with paired t-test, mean±SEM *$p<0.05$. These data indicate that NGAL mediates the apoptotic response of SEB-1 sebocytes to 13-cis RA.

Example 11

SEB-1 Sebocytes Express the Receptor for NGAL

A cell surface receptor for the murine homolog to NGAL, 24p3, was identified in murine pro-B lymphocytic FL5.12 cells. The presence of this receptor (24p3R) is believed to be responsible for cell-specific susceptibility to apoptosis (6). Based on sequence homology, the human homolog of 24p3R is predicted to be the solute carrier member, SLC22A17 (6). Expression of SLC22A17 mRNA was detected in SEB-1 sebocytes by QPCR analysis (data not shown).

24p3R (NGAL receptor) affinity purified antibody (6) was used. SEB-1 sebocytes were cultured and fixed according to standard procedures followed by overnight incubation with 24p3R antibody or normal rabbit IgG (negative control) and counterstaining with hematoxylin.

The 24p3/NGAL receptor was detected in SEB-1 sebocytes by immunohistochemistry and western blotting using an antibody to the mouse 24p3R(6).

Figure 8:
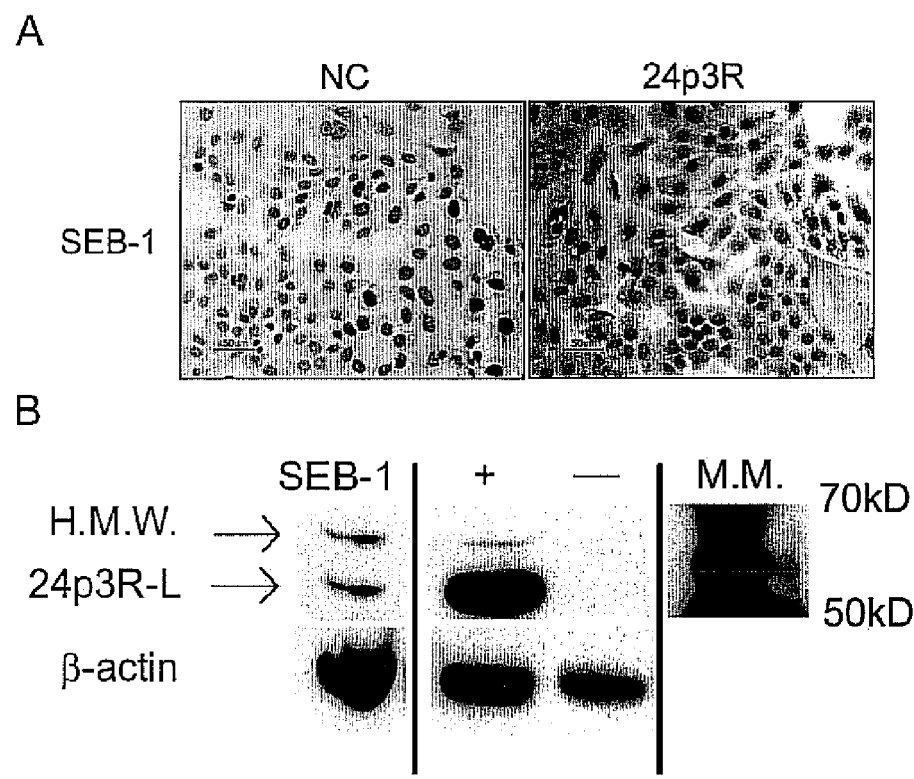
FIG. 8A is a reproduction of images of SEB-1 sebocytes immunostained using an antibody to the murine 24p3 receptor (also known as the murine lipocalin 2 receptor and the murine NGAL receptor) showing presence of the receptor in cytoplasm of the cells.
FIG. 8B is a reproduction of an image of a Western blot analysis confirming presence of the murine 24p3 receptor in SEP-1 sebocytes and indicating two receptor isoforms are present in SEB-1 sebocytes.

FIGS. 8A and 8B show that SEB-1 sebocytes express the receptor for NGAL. FIG. 8A shows results of experiments in which SEB-1 sebocytes were grown under standard conditions and immunocytochemistry was performed using an antibody to the murine 24p3 receptor. Slides were counterstained with hematoxylin. Negative control (NC) was processed with normal rabbit IgG antibody in place of the primary antibody. Magnification bar indicates 50 µm. Immunoreactivity for the 24p3 receptor localizes to the cytoplasm of SEB-1 sebocytes.

Western analysis confirms presence of the receptor and indicates two receptor isoforms are present in SEB-1 sebocytes: high molecular weight (H.M.W.) and 24p3R long (24p3R-L). Positive ((+); HEK 293 cell lysate) and negative ((−); T47D cell lysate) controls are shown in FIG. 5B. All samples for this blot were run on the same gel but were noncontiguous. Blot shown is representative of 3 independent experiments.

Example 12

*P. acnes* induces NGAL expression through TLR2 signaling.

Figure 9:
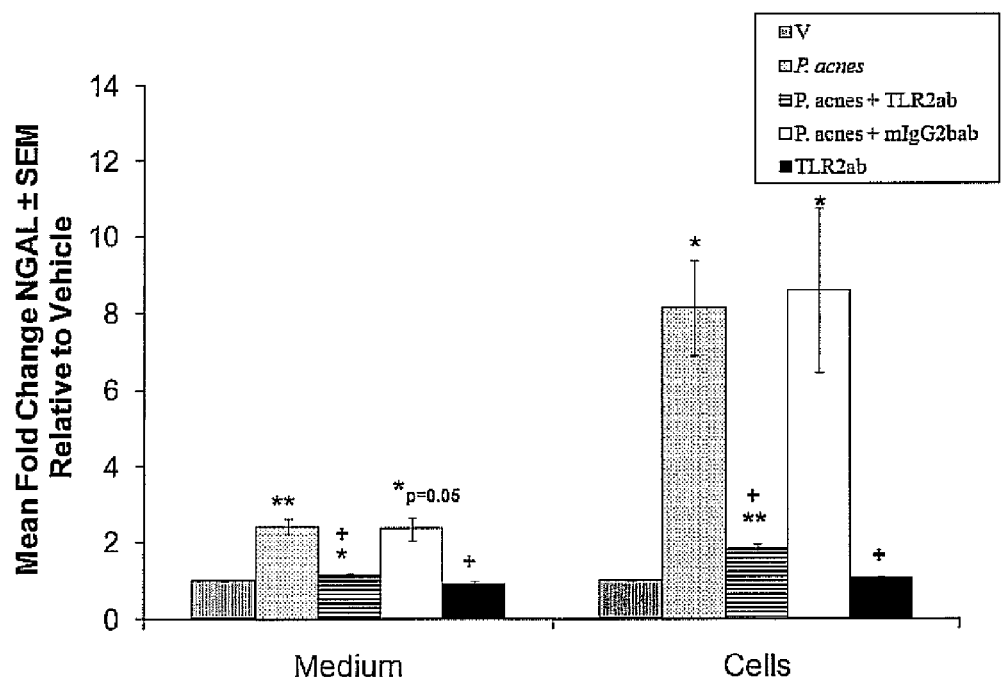
FIG. 9 is a graph showing that NGAL expression is significantly increased through Toll-like receptor 2 signaling.

SEB-1 sebocytes are pretreated with TLR2 neutralizing antibody, or corresponding isotype control antibody (mIgG2b) for one hour prior to treatment with 30 µg/mL *P. acnes*, vehicle or with TLR2 antibody alone for 24 hours. An ELISA assay for NGAL is performed on culture medium and the cell lysates. Data is analyzed using a paired Student's t-test n=4 *$p<0.05$. FIG. 9 is a graph showing that, in the presence of *P. acnes*, NGAL expression is significantly increased in both the culture medium and within cells when compared to vehicle and that, in the presence of TLR2 neutralizing antibody, *P. acnes* induced NGAL expression decreases; close to vehicle levels.

Example 13

Figure 10:
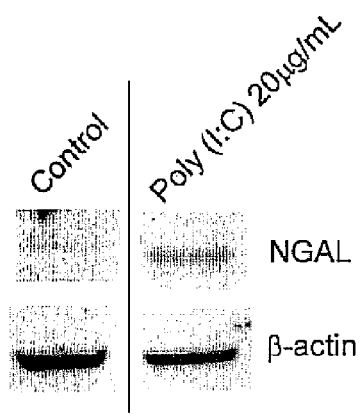
FIG. 10 is a reproduction of images of immunoblots for NGAL indicating that NGAL expression increases in response to poly (I:C) treatment.
Figure 11:
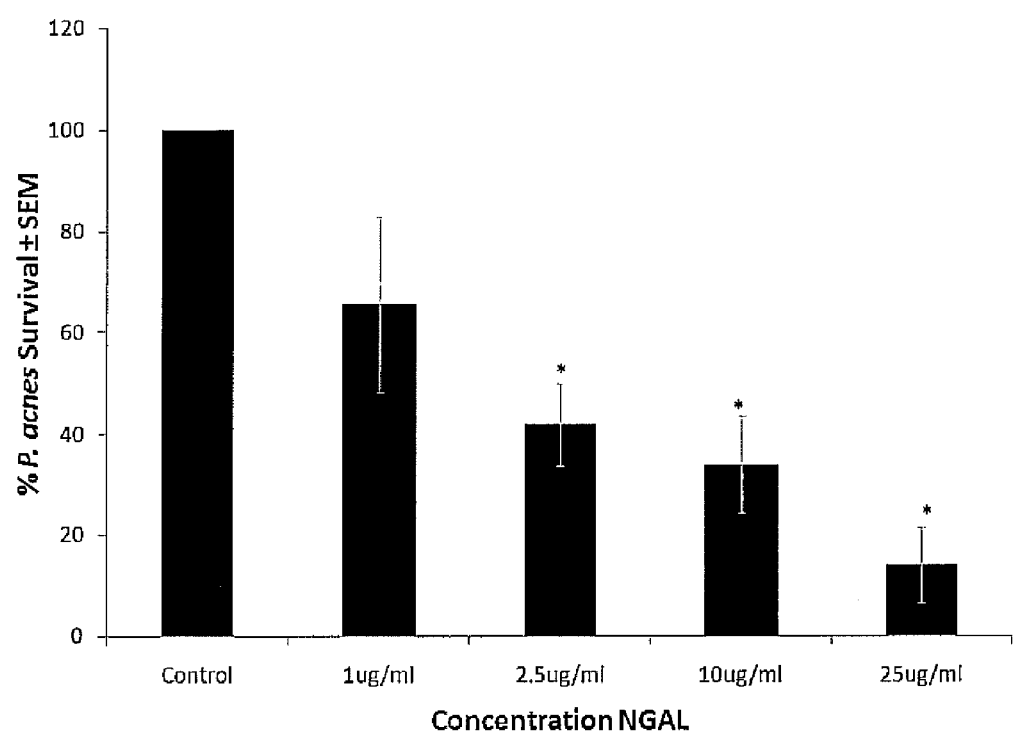
FIG. 11 is a graph showing inhibitory effects of NGAL oar *P. acnes* bacteria.

NGAL expression increases in response to poly (I:C) treatment in SEB-1 sebocytes. SEB-1 sebocytes are treated with 20 µg/mL Poly (I:C), commercially available from Invivogen, San Diego, Calif., for 48 hrs. Total cell lysate is examined for NGAL expression by immunoblotting. Samples are run on same gel. FIG. 10 shows immunoblots for NGAL and the control, beta-actin, indicating that NGAL expression increases in response to poly (I:C) treatment in SEB-1 sebocytes.

Example 14

*P. acnes* bacterium is treated with varying concentrations of recombinantly produced human NGAL (rhNGAL) produced in *E. coli* (1-25 µg/mL) for 4 hours. Dilutions are plated and the percent survival is calculated relative to vehicle. Both apo-NGAL (not bound to iron) and holo-NGAL (iron bound) are produced in *E. coli* and are easily distinguishable from one another due to the fact that holo-NGAL has pink hue when purified and apo-NGAL does not.

TABLE V

Significantly Changed genes after one-week Isotretinoin treatment.

| Probe ID | Accession # | Fold Δ | Gene Title | Symbol |
|---|---|---|---|---|
| 212531_at | NM_005564 | .03 | lipocalin 2 (oncogene 24p3) | LCN2 |
| 205916_at | NM_002963 | .20 | S100 calcium binding protein A7 (psoriasin 1) | S100A7 |
| 203535_at | NM_002965 | .53 | S100 calcium binding protein A9 (calgranulin B) | S100A9 |
| 219874_at | NM_024628 | .78 | solute carrier family 12 (K/Cl transporters) | SLC12A8 |
| 206754_s_at | NM_000767 | .32 | cytochrome P450, family 2, subfamily B | CYP2B7P1 |
| 202376_at | NM_001085 | .61 | serine (or cysteine) proteinase inhibitor | SERPINA3 |
| 206392_s_at | NM_002888 | .61 | retinoic acid receptor responder (TIG 1) | RARRES1 |
| 221872_at | AI669229 | .45 | retinoic acid receptor responder (TIG 1) | RARRES1 |
| 206391_at | NM_002888 | .42 | retinoic acid receptor responder (TIG 1) | RARRES1 |
| 218960_at | NM_016425 | .35 | transmembrane protease, serine 4 | TMPRSS4 |
| 206478_at | NM_014792 | .27 | KIAA0125 | KIAA0125 |
| 219014_at | NM_016619 | .21 | placenta-specific 8 | PLAC8 |
| 219554_at | NM_016321 | .08 | Rhesus blood group, C glycoprotein | RHCG |
| 221605_s_at | AF136970 | .04 | pipecolic acid oxidase | PIPOX |
| 204351_at | NM_005980 | .99 | S100 calcium binding protein P | S100P |
| 218498_s_at | NM_014584 | .96 | ERO1-like (*S. cerevisiae*) | ERO1L |
| 207307_at | NM_001676 | .92 | ATPase, H+/K+ transporting, nongastric, alpha | ATP12A |
| 216598_s_at | S69738 | .91 | chemokine (C-C motif) ligand 2 | CCL2 |
| 203423_at | NM_002899 | .81 | retinol binding protein 1, cellular | RBP1 |
| 219795_at | NM_007231 | .69 | solute carrier family 6 (amino acid transporter) | SLC6A14 |
| 210827_s_at | U73844 | .67 | E74-like factor 3 (ets domain transcription factor) | ELF3 |
| 221701_s_at | AF352728 | .62 | stimulated by retinoic acid gene 6 homolog | STRA6 |
| 204541_at | NM_012429 | .57 | SEC14-like 2 (*S. cerevisiae*) | SEC14L2 |
| 202575_at | NM_001878 | .56 | cellular retinoic acid binding protein 2 | CRABP2 |
| 210397_at | U73945 | .52 | defensin, beta 1 | DEFB1 |
| 205428_s_at | NM_001740 | .51 | calbindin 2, 29 kDa (calretinin) | CALB2 |
| 204268_at | NM_005978 | .50 | S100 calcium binding protein A2 | S100A2 |
| 214088_s_at | AW080549 | .49 | fucosyltransferase 3 | FUT3 |
| 214599_at | NM_005547 | .49 | involucrin | IVL |
| 205926_at | NM_004843 | .49 | interleukin 27 receptor, alpha | IL27RA |
| 219578_s_at | AF329403 | .48 | cytoplasmic polyadenylation element BP 1 | CPEB1 |
| 216379_x_at | AK000168 | .43 | CD24 antigen | CD24 |
| 221577_x_at | BC000529 | .41 | growth differentiation factor 15 | GDF15 |
| 213316_at | AL050154 | .40 | KIAA1462 | KIAA1462 |
| 205185_at | NM_006846 | .39 | serine protease inhibitor, Kazal type 5 | SPINK5 |
| 219956_at | NM_007210 | .38 | UDP-N-acetyl-alpha-D-galactosamine | GALNT6 |
| 212715_s_at | AB020626 | .27 | microtubule associated monoxygenase | MICAL3 |
| 218963_s_at | NM_015515 | .26 | keratin 23 (histone deacetylase inducible) | KRT23 |
| 206143_at | NM_000111 | 2.29 | solute carrier family 26, member 3 | SLC26A3 |
| 206214_at | NM_005084 | 2.27 | phospholipase A2, group VII (PAF acetylhydrolase) | PLA2G7 |
| 206623_at | NM_000440 | 2.13 | phosphodiesterase 6A, cGMP-specific, rod, alpha | PDE6A |
| 206100_at | NM_001874 | 1.55 | carboxypeptidase M | CPM |
| 207030_s_at | NM_001321 | 1.50 | cysteine and glycine-rich protein 2 | CSRP2 |

TABLE VI

Significantly Changed genes in SEB-1 sebocytes after 72 hrs 13-cis RA

| Probe ID | Accession # | Fold Δ | Gene Title | Symbol |
|---|---|---|---|---|
| 1042_at | U27185 | 12.25 | retinoic acid receptor responder (tazarotene induced) 1 | RARRES1 |
| 33505_at | AI887421 | 9.89 | retinoic acid receptor responder (tazarotene induced) 1 | RARRES1 |
| 32821_at | AI762213 | 7.04 | lipocalin 2 (oncogene 24p3) | LCN2 |
| 38631_at | M92357 | 5.95 | tumor necrosis factor, alpha-induced protein 2 | TNFAIP2 |
| 32570_at | L76465 | 5.91 | hydroxyprostaglandin dehydrogenase 15-(NAD) | HPGD |
| 36105_at | M18728 | 4.98 | carcinoembryonic antigen-related cell adhesion molecule 6 (non-specific cross reacting antigen) | CEACAM6 |
| 40071_at | U03688 | 4.64 | cytochrome P450, family 1, subfamily B, polypeptide 1 | CYP1B1 |
| 859_at | U03688 | 4.30 | cytochrome P450, family 1, subfamily B, polypeptide 1 | CYP1B1 |
| 37322_s_at | X82460 | 4.25 | hydroxyprostaglandin dehydrogenase 15-(NAD) | HPGD |
| 1715_at | U37518 | 4.18 | tumor necrosis factor (ligand) superfamily, member 10 | TNFSF10 |
| 1343_s_at | S66896 | 3.70 | serine (or cysteine) proteinase inhibitor, clade B (ovalbumin), member 3 | SERPINB3 |
| 873_at | M26679 | 3.65 | homeo box A5 | HOXA5 |

TABLE VI-continued

Significantly Changed genes in SEB-1 sebocytes after 72 hrs 13-cis RA

| Probe ID | Accession # | Fold Δ | Gene Title | Symbol |
|---|---|---|---|---|
| 988_at | X16354 | 3.52 | carcinoembryonic antigen-related cell adhesion molecule 1 (biliary glycoprotein) | CEACAM1 |
| 1586_at | M35878 | 3.43 | insulin-like growth factor binding protein 3 | IGFBP3 |
| 36686_at | U07919 | 3.29 | aldehyde dehydrogenase 1 family, member A3 | ALDH1A3 |
| 33236_at | AF060228 | 3.22 | retinoic acid receptor responder (tazarotene induced) 3 | RARRES3 |
| 37233_at | AF079167 | 3.08 | oxidised low density lipoprotein (lectin-like) receptor 1 | OLR1 |
| 36609_at | D26443 | 3.06 | solute carrier family 1 (glial high affinity glutamate transporter), member 3 | SLC1A3 |
| 1890_at | AB000584 | 3.00 | growth differentiation factor 15 | GDF15 |
| 33131_at | X70683 | 2.98 | SRY (sex determining region Y)-box 4 | SOX4 |
| 35064_at | X81006 | 2.74 | tripartite motif-containing 31 | TRIM31 |
| 2031_s_at | U03106 | 2.60 | cyclin-dependent kinase inhibitor 1A (p21, Cip1) | CDKN1A |
| 40445_at | AF017307 | 2.51 | E74-like factor 3 (ets domain transcription factor, epithelial-specific) | ELF3 |
| 37821_at | AF041260 | 2.48 | breast carcinoma amplified sequence 1 | BCAS1 |
| 37533_r_at | D86980 | 2.46 | tetratricopeptide repeat domain 9 | TTC9 |
| 669_s_at | L05072 | 2.42 | interferon regulatory factor 1 | IRF1 |
| 38584_at | AF026939 | 2.42 | interferon-induced protein with tetratricopeptide repeats 3 | IFIT3 |
| 35029_at | Y07828 | 2.35 | tripartite motif-containing 31 | TRIM31 |
| 41814_at | M29877 | 2.29 | fucosidase, alpha-L- 1, tissue | FUCA1 |
| 909_g_at | M14660 | 2.23 | interferon-induced protein with tetratricopeptide repeats 2 | IFIT2 |
| 36634_at | U72649 | 2.20 | BTG family, member 2 | BTG2 |
| 908_at | M14660 | 2.20 | interferon-induced protein with tetratricopeptide repeats 2 | IFIT2 |
| 1582_at | M29540 | 2.18 | carcinoembryonic antigen-related cell adhesion molecule 5 | CEACAM5 |
| 384_at | X71874 | 2.09 | proteasome (prosome, macropain) subunit, beta type, 10 | PSMB10 |
| 41433_at | M73255 | 2.08 | vascular cell adhesion molecule 1 | VCAM1 |
| 39669_at | AJ009985 | 2.07 | annexin A9 | ANXA9 |
| 38389_at | X04371 | 2.07 | 2',5'-oligoadenylate synthetase 1, 40/46 kDa | OAS1 |
| 1882_g_at | HG4058-HT4328 | 2.06 | — | — |
| 33559_at | U61412 | 1.94 | PTK6 protein tyrosine kinase 6 | PTK6 |
| 40511_at | X58072 | 1.85 | GATA binding protein 3 | GATA3 |
| 38388_at | M11810 | 1.82 | 2',5'-oligoadenylate synthetase 1, 40/46 kDa | OAS1 |
| 38042_at | X03674 | 1.79 | protein kinase C, alpha | PRKCA |
| 902_at | L41939 | 1.78 | EPH receptor B2 | EPHB2 |
| 34162_at | D84111 | 1.78 | RNA binding protein with multiple splicing | RBPMS |
| 38269_at | AL050147 | 1.77 | protein kinase D2 | PRKD2 |
| 38242_at | AF068180 | 1.76 | B-cell linker | BLNK |
| 37383_f_at | X58536 | 1.71 | major histocompatibility complex, class I, B /// major histocompatibility complex, class I, C | HLA-B /// HLA-C |
| 39665_at | U33267 | 1.71 | glycine receptor, beta | GLRB |
| 881_at | M35198 | 1.71 | integrin, beta 6 | ITGB6 |
| 544_at | 576638 | 1.70 | nuclear factor of kappa light polypeptide gene enhancer in B-cells 2 (p49/p100) | NFKB2 |
| 37643_at | X63717 | 1.69 | Fas (TNF receptor superfamily, member 6) | FAS |
| 33267_at | AF035315 | 1.66 | ATPase, aminophospholipid transporter (APLT), Class I, type 8A, member 1 | ATP8A1 |
| 1562_g_at | U27193 | 1.66 | dual specificity phosphatase 8 | DUSP8 |
| 37451_at | AL109695 | 1.62 | solute carrier organic anion transporter family, member 3A1 | SLCO3A1 |
| 35194_at | X53463 | 1.60 | glutathione peroxidase 2 (gastrointestinal) | GPX2 |
| 34213_at | AB020676 | 1.59 | KIBRA protein | KIBRA |
| 40898_at | U46751 | 1.56 | sequestosome 1 | SQSTM1 |
| 322_at | D88532 | 1.47 | phosphoinositide-3-kinase, regulatory subunit 3 (p55, gamma) | PIK3R3 |
| 39015_f_at | L42611 | −4.76 | keratin 6A /// keratin 6C | KRT6A KRT6C |
| 34721_at | U42031 | −4.00 | FK506 binding protein 5 | FKBP5 |
| 39016_r_at | L42611 | −3.85 | keratin 6A /// keratin 6C | KRT6A KRT6C |
| 33821_at | AL034374 | −3.23 | ELOVL family member 5, elongation of long chain fatty acids (FEN1/Elo2, SUR4/Elo3-like, yeast) | ELOVL5 |
| 1610_s_at | J00139 | −3.12 | dihydrofolate reductase | DHFR |
| 32005_at | M57703 | −2.78 | pro-melanin-concentrating hormone | PMCH |
| 39681_at | AF060568 | −2.70 | zinc finger and BTB domain containing 16 | ZBTB16 |

TABLE VI-continued

Significantly Changed genes in SEB-1 sebocytes after 72 hrs 13-cis RA

| Probe ID | Accession # | Fold Δ | Gene Title | Symbol |
|---|---|---|---|---|
| 36739_at | U54617 | −2.56 | pyruvate dehydrogenase kinase, isoenzyme 4 | PDK4 |
| 31691_g_at | U08997 | −2.50 | glutamate dehydrogenase 1 | GLUD1 |
| 36922_at | X59618 | −2.27 | ribonucleotide reductase M2 polypeptide | RRM2 |
| 32251_at | AA149307 | −2.27 | transcription elongation factor A (SII)-like 4 | TCEAL4 |
| 36270_at | U04343 | −2.13 | CD86 antigen (CD28 antigen ligand 2, B7-2 antigen) | CD86 |
| 39677_at | D80008 | −2.04 | DNA replication complex GINS protein PSF1 | PSF1 |
| 40137_at | M31724 | −2.04 | protein tyrosine phosphatase, non-receptor type 1 | PTPN1 |
| 34944_at | U51704 | −2.04 | — | — |
| 39153_r_at | U06632 | −1.96 | coilin | COIL |
| 779_at | D21337 | −1.92 | collagen, type IV, alpha 6 | COL4A6 |
| 37062_at | S62907 | −1.92 | gamma-aminobutyric acid (GABA) A receptor, alpha 2 | GABRA2 |
| 32283_at | AI239869 | −1.89 | Iduronate 2-sulfatase | MPS2 |
| 39338_at | AI201310 | −1.82 | S100 calcium binding protein A10 (annexin II ligand, calpactin I, light polypeptide (p11)) | S100A10 |
| 115_at | X14787 | −1.79 | thrombospondin 1 | THBS1 |
| 36104_at | AA526497 | −1.79 | ubiquinol-cytochrome c reductase hinge protein | UQCRH |
| 35938_at | M72393 | −1.79 | phospholipase A2, group IVA (cytosolic, calcium-dependent) | PLA2G4A |
| 35342_at | AF052159 | −1.72 | protein tyrosine phosphatase-like (proline instead of catalytic arginine), member b | PTPLB |
| 1536_at | U77949 | −1.64 | CDC6 cell division cycle 6 homolog (S. cerevisiae) | CDC6 |
| 41547_at | AF047472 | −1.59 | BUB3 budding uninhibited by benzimidazoles 3 homolog (yeast) | BUB3 |
| 41529_g_at | W72239 | −1.49 | hypothetical protein LOC130074 | LOC130074 |

REFERENCES

1. Reynolds, C. P., Matthay, K. K., Villablanca, J. G., and Maurer, B. J. 2003. Retinoid therapy of high-risk neuroblastoma. Cancer Let 197:185-192.
2. Landthaler, M., Kummermehr, J., Wagner, A., and Plewig, G. 1980. Inhibitory effects of 13-cis reinoic acid on human sebaceous glands. Arch Dermatol 269:297-3069.
3. Strauss, J. S., Stranieri, A. M., Farrell, L. N., and Downing, D. T. 1980. The effect of marked inhibition of sebum production with 13-cis retinoic acid on skin surface lipid composition. J Invest Dermatol 74:66-67.
4. Goldstein, J. A., Comite, H., Mescon, H., and Pochi, P. E. 1982. Isotretinoin in the treatment of Acne. Arch Dermatol 118:555-558.
5. Peck, G. L. 1979. Prolonged remissions of cystic acne with 13-cis retinoic acid. N Engl J Med 300:329.
6. Devireddy, L. R., Gazin, C., Zhu, X., and Green, M. R. 2005. A cell-surface receptor for lipocalin 24p3 selectively mediates apoptosis and iron uptake. Cell 123:1293-1305.
7. Flo, T. H., Smith, K. D., Sato, S., Rodriguez, I. J., Holmes, M. A., Strong, R. K., Akira, S., and Aderem, A. 2004. Lipocalin 2 mediates an innate immune response to bacterial infection by sequestrating iron. Nature 432:917-921.
8. Nelson, A. M., Gilliland, K. L., Cong, Z., and Thiboutot, D. M. 2006. 13-cis Retinoic acid induces apoptosis and cell cycle arrest in human SEB-1 sebocytes. J Invest Dermatol 126:2178-2189.
9. Shen, F., Hu, Z., Goswami, J., and Gaffen, S. L. 2006. Identification of common transcriptional regulatory elements in interleukin-17 target genes. J Biol Chem 281:24138-24148.
10. Yoneyama, M., Kikuchi, M., Natsukawa, T., Shinobu, N., Imaizumi, T., Miyagishi, M., Taira, K., Akira, S., and Fujita, T. 2004. The RNA helicase RIG-I has an essential function in double-stranded RNA-induced innate antiviral responses. Nat Immunol 5:730-737.
11. Sen, G. C., and Sarkar, S. N. 2005. Hitching RIG to action. Nat Immunol 6:1074-1076.
12. Tsukada, M., Schroder, M., Roos, T. C., Chandraratna, R. A., Reichert, U., Merk, H. F., Orfanos, C. E., and Zouboulis, C. C. 2000. 13-cis retinoic acid exerts its specific activity on human sebocytes through selective intracellular isomerization to all-trans retinoic acid and binding to retinoid acid receptors. J Invest Dermatol 115:321-327.
13. Ochoa, W. F., Torrecillas, A., Fita, I., Verdaguer, N., Corbalan-Garcia, S., and Gomez-Fernandez, J. C. 2003. Retinoic acid binds to the C2-domain of protein kinase C(alpha). Biochemistry 42:8774-8779.
14. Pettersson, F., Couture, M.-C. Hanna, N., and Miller Jr., W. 2004. Enhanced retinoid-induced apoptosis of MDA-MB-231 breast cancer cells by PKC inhibitors involved activation of ERIC. Oncogene 23:7053-7066.
15. White, G. M. 1998. Recent findings in the epidemiologic evidence, classification, and subtypes of acne vulgaris. J Am Acad Dermatol 39:$34-37.
16. Bickers, D. R., Lim, H. W., Margolis, D., Weinstock, M. A., Goodman, C., Faulkner, E., Gould, C., Gemmen, E., and Dall, T. 2006. The burden of skin diseases: 2004: A joint project of the American Academy of Dermatology Association and the Society for Investigative Dermatology. J Am Acad Dermatol 55:490-500.
17. Kim, J., Ochoa, M., Krutzik, S., Takeuchi, O., Uematsu, S., Legaspi, A., Brightbill, H., Holland, D. B., Cunliffe, W. J., Akira, S., et al. 2002. Activation of toll-like receptor 2 in acne triggers inflammatory cytokine responses. J Immunol 169:1535-1541.

18. Zouboulis, C. C., Zia, L., Korge, B., Gollnick, H., and Orfanos, C. E. 1991. Cultivation of Human Sebocytes in vitro: Cell Characterization and Influence of Synthetic Retinoids. In Retinoids: 10 Years On. J.-H. Saurat, editor: Basel, Karger. pp. 254-273.
19. Zouboulis, C. C., Korge, B., Akamatsu, H., Xia, L. Q., Schiller, S., Gollnick, H., and Orfanos, C. E. 1991. Effects of 13-cis retinoic acid, all-trans-retinoic acid, and acitretin on the proliferation, lipid synthesis and keratin expression of cultured human sebocytes in vitro. J Invest Dermatol 96:792-797.
20. Zouboulis, C. C., Seltmann, H., Neitzel, H., and Orfanos, C. E. 1999. Establishment and characterization of an immortalized human sebaceous gland cell line (SZ95). Invest Dermatol 113:1011-1020.
21. Gomez, E. C., and Moskowitz, R. J. 1980. Effect of 13-cis retinoic acid on the hamster flank organ. J Invest Dermatol 74:392-397.
22. Goldstein, J. A., Socha-Szott, A., Thomsen, R. J., Pochi, P. E., Shalita, A. R., and Strauss, J. S. 1982. Comparative effect of isotretinoin and etretinate on acne and sebaceous gland secretion. J Am Acad Dermatol 6:760-765.
23. Newcomer, M. E., and Ong, D. E. 2000. Plasma retinol binding protein: structure and function of the prototypic lipocalin. Biochim Biophys Acta 1482:57-64.
24. Yang, J., Goetz, D., Li, J. Y., Wang, W., Mori, K., Setlik, D., Du, T., Erdjument-Bromage, H., Tempst, P., Strong, R., et al. 2002. An iron delivery pathway mediated by a lipocalin. Mol Cell 10:1045-1056.
25. Hanai, J., Mammoto, T., Seth, P., Mori, K., Karumanchi, S. A., Barasch, J., and Sukhatme, V. P. 2005. Lipocalin 2 diminishes invasiveness and metastasis of Ras-transformed cells. J Biol Chem 280:13641-13647.
26. Mishra, J., Ma, Q., Prada, A., Mitsnefes, M., Zabedi, K., Yang, J., Barasch, J., and Devarajan, P. 2003. Identification of neutrophil gelatinase-associated lipocalin as a novel early urinary biomarker for ischemic renal injury. J Am Soc Nephrol 14:2534-2543.
27. Kjeldsen, L., Bainton, D. F., Sengelov, H., and Borregaard, N. 1994. Identification of neutrophil gelatinase-associated lipocalin as a novel matrix protein of specific granules in human neutrophils. Blood 83:799-807.
28. Yan, L., Borregaard, N., Kjeldsen, L., and Moses, M. A. 2001. The high molecular weight urinary matrix metalloproteinase (MMP) activity is a complex of gelatinase B/MMP-9 and neutrophil gelatinase-associated lipocalin (NGAL). Modulation of MMP-9 activity by NGAL. J Biol Chem 276:37258-37265.
29. Akerstrom, B., Flower, D. R., and Salier, J. P. 2000. Lipocalins: unity in diversity. Biochim Biophys Acta 1482: 1-8.
30. Logdberg, L., and Wester, L. 2000. Immunocalins: a lipocalin subfamily that modulates immune and inflammatory responses. Biocliim Biophys Acta 1482:284-297.
31. Seo, S. J., Ahn, J. Y., Hong, C. K., Seo, E. Y., Kye, K. C., Lee, W. E., Lee, S. K., Lim, J. S., Halin, M. J., Kjeldsen, L., et al. 2006. Expression of neutrophil gelatinase-associated lipocalin in skin epidermis. J Invest Dermatol 126:510-512.
32. Mallbris, L., O'Brien, K. P., Hulthen, A., Sandstedt, B., Cowland, J. B., Borregaard, N., and Stahle-Backdahl, M. 2002. Neutrophil gelatinase-associated lipocalin is a marker for dysregulated keratinocyte differentiation in human skin. Exp Dermatol 11:584-591.
33. Lin, H. H., Li, W. W., Lee, Y. C., and Chu, S. T. 2007. Apoptosis induced by uterine 24p3 protein in endometrial carcinoma cell line. Toxicology 234:203-215.
34. Li, P. T., Lee, Y. C., Elangovan, N., and Chu, S. T. 2007. Mouse 24p3 protein has an effect on L929 cell viability. Int J Biol Sci 3:100-107.
35. Nagpal, S., Patel, S., Asano, A., Johnson, A., Duvic, M., and Chandraratna, R. 1996. TIG1 and TGI2 (tazarotene-induced genes 1 and 2) are novel retinoic acid receptor responsive genes in skin. J Invest Dermatol 106:818.
36. DiSepio, D., Ghosn, C., Eckert, R. L., Deucher, A., Robinson, N., Duvic, M., Chandraratna, R. A., and Nagpal, S. 1998. Identification and characterization of a retinoid-induced class IL tumor suppressor/growth regulatory gene. Proc Natl Acad Sci USA 95:14811-14815.
37. Caramuta, S., De Cecco, L., Reid, J. F., Zannini, L., Gariboldi, M., Kjeldsen, L., Pierotti, M. A., and Delia, D. 2006. Regulation of lipocalin-2 gene by the cancer chemopreventive retinoid 4-HPR. Int J Cancer 119:1599-1606.
38. Levin, A., Bosakowski, T., Kazmer, S., and Grippo, J. F. 1992. 13-cis Retinoic Acid does not bind to retinoic acid receptors alpha, beta and gamma. Toxicologist 12:181.
39. Allenby, G., Bocquel, M. T., Saunders, M., Kazmer, S., Speck, J., Rosenberger, M., Lovey, A., Kastner, P., Grippo, J. F., Chambon, P., et al. 1993. Retinoic acid receptors and retinoid X receptors: interactions with endogenous retinoic acids. Proc Natl Acad Sci USA 90:30-34.
40. Baron, J. M., Heise, R., Blaner, W. S., Neis, M., Joussen, S., Dreuw, A., Marquardt, Y., Saurat, J. H., Merk, H. F., Bickers, D. R., et al. 2005. Retinoic Acid and its 4-Oxo Metabolites are Functionally Active in Human Skin Cells In Vitro. J Invest Dermatol 125:143-153.
41. Kjeldsen, L., Cowland, J. B., and Borregaard, N. 2000. Human neutrophil gelatinase-associated lipocalin and homologous proteins in rat and mouse. Biochim Biophys Acta 1482:272-283.
42. Draper, D. W., Bethea, M. N., and He, Y. W. 2006. Toll-like receptor 2-dependent and -independent activation of macrophages by group B streptococci. Immunol Lett 102: 202-214.
43. Cowland, J. B., Sorensen, O. E., Sehested, M. and Borregaard, N. 2003. Neutrophil gelatinase-associated lipocalin is up-regulated in human epithelial cells by IL-1 beta, but not by TNF-alpha. J Immunol 171:6630-6639.
44. Fujino, R. S., Tanalka, K., Morimatsu, M., Tamura, K., Kogo, H., and Hara, T. 2006. Spermatogonial cell-mediated activation of an IkappaBzeta-independent nuclear factor-kappaB pathway in Sertoli cells induces transcription of the lipocalin-2 gene. Mol Endocrinol 20:904-915.
45. Ziegler, S., Rohrs, S., Tickenbrock, L., Langerak, A., Chu, S. T., Feldmann, I., Jakubowski, N., and Muller, O. 2007. Lipocalin 24p3 is regulated by the Wnt pathway independent of regulation by iron. Cancer Genet Cytogenet 174: 16-23.
46. Florin, L., Hummerich, L., Dittrich, B. T., Kokocinski, F., Wrobel, G., Gack, S., Schorpp-Kistner, M., Werner, S., Hahn, M., Lichter, P., et al. 2004. Identification of novel AP-1 target genes in fibroblasts regulated during cutaneous wound healing. Oncogene 23:7005-7017.
47. Trivedi, N. R., Gilliland, K. L., Zhao, W., Liu, W., and Thiboutot, D. M. 2006. Gene array expression profiling in acne lesions reveals marked upregulation of genes involved in inflammation and matrix remodeling. J invest Dermatol 126:1071-1079.
48. Jugeau, S., Tenaud, I., Knol, A. C., Jarrousse, V., Quereux, G., Khammari, A., and Dreno, B. 2005. Induction of toll-like receptors by *Propionibacterium acnes*. Br J Dermatol 153:1105-1113.
49. Leyden, J. J., McGinley, K. J., and Foglia, A. N. 1986. Qualitative and quantitative changes in cutaneous bacteria associated with systemic isotretinoin therapy for acne conglobata. J Invest Dermatol 86:390-393.
50. Coates, P., Vyakrnam, S., Ravenscroft, J. C., Stables, G. I., Cunliffe, W. J., Leyden, J. J., Johnson, J., Eady, E. A., and Cove, J. H. 2005. Efficacy of oral isotretinoin in the control of skin and nasal colonization by antibiotic-resistant propionibacteria in patients with acne. Br J Dermatol 153: 1126-1136.
51. Kawaguchi, M., Adachi, M., Oda, N., Kokubu, F., and Huang, S. K. 2004. IL-17 cytokine family. J Allergy Clin Immunol 114:1265-1273; quiz 1274.
52. Li, J., Chen, X., Liu, Z., Yue, Q., and Liu, H. 2007. Expression of Th17 cytokines in skin lesions of patients with psoriasis. J Huazhong Univ Sci Technolog Med Sci 27:330-332.
53. Lubberts, E., Joosten, L. A., Oppers, B., van den Bersselaar, L., Coenen-de Roo, C. J., Kolls, J. K., Schwarzenberger, P., van de Loo, F. A., and van den Berg, W. B. 2001. IL-1-independent role of IL-17 in synovial inflammation and joint destruction during collagen-induced arthritis. 3 Immunol 167:1004-1013.
54. Kang, S., Cho, S., Chung, J. H., Hammerberg, C., Fisher, G. J., and Voorhees, J. J. 2005. Inflammation and extracellular matrix degradation mediated by activated transcription factors nuclear factor-kappaB and activator protein-1 in inflammatory acne lesions in vivo. Am J Pathol 166: 1691-1699.
55. Eckert, R. L., Broome, A. M., Ruse, M., Robinson, N., Ryan, D., and Lee, K. 2004. S100 proteins in the epidermis. J Invest Dermatol 123:23-33.
56. Silverman, G. A., Bird, P. I., Carrell, R. W., Church, F. C., Coughlin, P. B., Gettins, P. G., Irving, J. A., Lomas, D. A., Luke, C. J., Moyer, R. W., et al. 2001. The serpins are an expanding superfamily of structurally similar but functionally diverse proteins. Evolution, mechainism of inhibition, novel functions, and a revised nomenclature. J Biol Chem 276:33293-33296.
57. Glaser, R., Harder, J., Lange, H., Bartels, J., Christophers, E., and Schroder, J. M. 2005. Antimicrobial psoriasin (S100A7) protects human skin from *Escherichia coli* infection. Nat Immunol 6:57-64.
58. Yamasaki, K., Di Nardo, A., Bardan, A., Murakami, M., Ohtake, T., Coda, A., Dorschner, R. A., Bonnart, C., Descargues, P., Hovnanian, A., et al. 2007. Increased serine protease activity and cathelicidin promotes skin inflammation in rosacea. Nat Med 13:975-980.
59. Thiboutot, D., Jabara, S., McAllister, J., Sivarajah, A., Gilliland, K., Cong, Z., and Clawson, G. 2003. Human skin is a steroidogenic tissue: Steroidogenic enzymes and cofactors are expressed in epidermis, normal sebocytes, and an immortalized sebocyte cell line (SEB-1). J Invest Dermatol 120:905-914.
60. Irizany, R. A., Gautier, L., and Cope, L. M. 2003. The Analysis of Gene Expression Data Methods and Software: Springer Verlag.
61. Irizarry, R. A., Hobbs, B., Collin, F., Beazer-Barclay, Y. D., Antonellis, K. J., Scherf, U., and Speed, T. P. 2003. Exploration, normalization, and summaries of high density oligonucleotide array probe level data. Biostatistics 4:249-264.
62. Tusher, V. G., Tibshirani, R., and Chu, G. 2001. Significance analysis of microarrays applied to the ionizing radiation response. Proc Natl Acad Sci USA 98:5116-5121.
63. Benjamini, Y., and Yekutieli, D. 2005. Quantitative trait Loci analysis using the false discovery rate. Genetics 171: 783-790.
64. Pfaffl, M. W., Horgan, G. W., and Dempfle, L. 2002. Relative expression software tool (REST) for group-wise comparison and statistical analysis of relative expression results in real-time PCR. Nucleic Acids Res 30:e36.
65. Kalali, B. N., Kollisch, C., Mages, J., et al. 2008. Double-stranded RNA induces an antiviral defense status in epidemial keratinocytes through TLR3-, PKR-, and MDA5/RIG-I-mediated differential signaling. *J Immunol* 181: 2694-2704.
66. Vijay-Kumar, M., Gentsch, J. R., Kaiser, W. J., et al. 2005. Protein kinase R mediates intestinal epithelial gene remodeling in response to double-stranded RNA and live rotavirus. *J Immunol* 174:6322-6331.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of treating acne in a subject, comprising: administering a therapeutically effective amount of an NGAL stimulator, wherein the NGAL stimulator is selected from the group consisting of: a Toll-like receptor 2 ligand, a Toll-like receptor 3 ligand, an activator of NFκB, leukotriene B4, cholesterol oleate and interleukin-17 (IL-17), to a subject having acne.

2. The method of claim 1, wherein the activator of NFκB is selected from the group consisting of: interleukin 1-beta (IL1-beta) and tumor necrosis factor-alpha (TNF-alpha).

3. The method of claim 1, wherein the Toll-like receptor 2 ligand is N-Palmitoyl-S-[2,3-bis(palmitoyloxy)-(2RS)-propyl]-[R]-cysteinyl-[S]-seryl-[S]-lysyl-N-lysyl-[S]-lysyl-[S]-lysine.

4. The method of claim 1, wherein the Toll-like receptor 3 ligand is polyinosinic:polycytidylic acid.

5. The method of claim 1, wherein the NGAL stimulator is administered to skin affected by acne in the subject.

\* \* \* \* \*

SEQUENCE LISTING

```
<160> NUMBER OF SEQ ID NOS: 4

<210> SEQ ID NO 1
<211> LENGTH: 198
<212> TYPE: PRT
<213> ORGANISM: human

<400> SEQUENCE: 1

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
    50                  55                  60
```

```
Asp Lys Asp Pro Gln Lys Met Tyr Ala Thr Ile Tyr Glu Leu Lys Glu
 65                  70                  75                  80

Asp Lys Ser Tyr Asn Val Thr Ser Val Leu Phe Arg Lys Lys Lys Cys
                 85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
            195

<210> SEQ ID NO 2
<211> LENGTH: 200
<212> TYPE: PRT
<213> ORGANISM: Mus musculus

<400> SEQUENCE: 2

Met Ala Leu Ser Val Met Cys Leu Gly Leu Ala Leu Leu Gly Val Leu
  1               5                  10                  15

Gln Ser Gln Ala Gln Asp Ser Thr Gln Asn Leu Ile Pro Ala Pro Ser
                 20                  25                  30

Leu Leu Thr Val Pro Leu Gln Pro Asp Phe Arg Ser Asp Gln Phe Arg
             35                  40                  45

Gly Arg Trp Tyr Val Val Gly Leu Ala Gly Asn Ala Val Gln Lys Lys
         50                  55                  60

Thr Glu Gly Ser Phe Thr Met Tyr Ser Thr Ile Tyr Glu Leu Gln Glu
 65                  70                  75                  80

Asn Asn Ser Tyr Asn Val Thr Ser Ile Leu Val Arg Asp Gln Asp Gln
                 85                  90                  95

Gly Cys Arg Tyr Trp Ile Arg Thr Phe Val Pro Ser Ser Arg Ala Gly
            100                 105                 110

Gln Phe Thr Leu Gly Asn Met His Arg Tyr Pro Gln Val Gln Ser Tyr
        115                 120                 125

Asn Val Gln Val Ala Thr Thr Asp Tyr Asn Gln Phe Ala Met Val Phe
130                 135                 140

Phe Arg Lys Thr Ser Glu Asn Lys Gln Tyr Phe Lys Ile Thr Leu Tyr
145                 150                 155                 160

Gly Arg Thr Lys Glu Leu Ser Pro Glu Leu Lys Glu Arg Phe Thr Arg
                165                 170                 175

Phe Ala Lys Ser Leu Gly Leu Lys Asp Asp Asn Ile Ile Phe Ser Val
            180                 185                 190

Pro Thr Asp Gln Cys Ile Asp Asn
            195                 200

<210> SEQ ID NO 3
<211> LENGTH: 840
<212> TYPE: DNA
<213> ORGANISM: human
```

```
<400> SEQUENCE: 3
actcgccacc tcctcttcca cccctgccag gcccagcagc caccacagcg cctgcttcct    60
cggccctgaa atcatgcccc taggtctcct gtggctgggc ctagccctgt tggggctct   120 gcatgcccag gcccaggact ccacctcaga cctgatccca gccccacctc tgagcaaggt   180
ccctctgcag cagaacttcc aggacaacca attccagggg aagtggtatg tggtaggcct   240
ggcagggaat gcaattctca gagaagacaa agacccgcaa aagatgtatg ccaccatcta   300
tgagctgaaa gaagacaaga gctacaatgt cacctccgtc ctgtttagga aaagaagtg    360 tgactactgg atcaggactt ttgttccagg ttgccagccc ggcgagttca cgctgggcaa   420
cattaagagt taccctggat taacgagtta cctcgtccga gtggtgagca ccaactacaa   480
ccagcatgct atggtgttct tcaagaaagt ttctcaaaac agggagtact caagatcac    540 cctctacggg agaaccaagg agctgacttc ggaactaaag gagaacttca tccgcttctc   600
caaatctctg ggcctccctg aaaaccacat cgtcttccct gtcccaatcg accagtgtat   660
cgacggctga gtgcacaggt gccgccagct gccgcaccag cccgaacacc attgagggag   720
ctgggagacc ctccccacag tgccacccat gcagctgctc cccaggccac cccgctgatg   780
gagccccacc ttgtctgcta aataaacatg tgccctcagg ccaaaaaaaa aaaaaaaaa    840

<210> SEQ ID NO 4
<211> LENGTH: 853
<212> TYPE: DNA
<213> ORGANISM: Mus musculus

<400> SEQUENCE: 4
agacctagta gctgtggaaa ccatggccct gagtgtcatg tgtctgggcc ttgccctgct    60
tggggtcctg cagagccagg cccaggactc aactcagaac ttgatccctg ccccatctct   120
gctcactgtc cccctgcagc cagacttccg gagcgatcag ttccggggca ggtggtacgt   180
tgtgggcctg gcaggcaatg cggtccagaa aaaaacagaa ggcagcttta cgatgtacag   240
caccatctat gagctacaag agaacaatag ctacaatgtc acctccatcc tggtcaggga   300
ccaggaccag ggctgtcgct actggatcag aacatttgtt ccaagctcca gggctggcca   360
gttcactctg ggaaatatgc acaggtatcc tcaggtacag agctacaatg tgcaagtggc   420
caccacggac tacaaccagt tcgccatggt atttttccga aagacttctg aaaacaagca   480
atacttcaaa attaccctgt atggaagaac caaggagctg tcccctgaac tgaaggaacg   540
tttcacccgc tttgccaagt ctctgggcct caaggacgaa aacatcatct tctctgtccc   600
caccgaccaa tgcattgaca actgaatggg tggtgagtgt ggctgactgg gatgcgcaga   660
gacccaatgg ttcaggcgct gcctgtctgt ctgccactcc atctttcctg ttgccagaga   720
gccacctggc tgccccacca gccaccatac caaggagcat ctggagcctc ttcttatttg   780
gccagcactc cccatccacc tgtcttaaca ccaccaatgg cgtcccctt ctgctgaata    840 aatacatgcc ccc                                                      853
```